(12) United States Patent
Moulton et al.

(10) Patent No.: US 10,031,114 B2
(45) Date of Patent: Jul. 24, 2018

(54) LIQUID-FREE SAMPLE TRAPS AND ANALYTICAL METHOD FOR MEASURING TRACE LEVEL ACIDIC AND BASIC AMC

(71) Applicant: Entegris, Inc., Billerica, MA (US)

(72) Inventors: Tyler Moulton, Grafton, MA (US); Jürgen M. Lobert, Franklin, MA (US); John C. Gaudreau, Chepachet, RI (US); Thomas Leblanc, Mendon, MA (US)

(73) Assignee: Entegris, Inc., Billerica, MA (US)

( * ) Notice: Subject to any disclaimer, the term of this patent is extended or adjusted under 35 U.S.C. 154(b) by 152 days.

(21) Appl. No.: 14/916,845

(22) PCT Filed: Sep. 5, 2014

(86) PCT No.: PCT/US2014/054266
§ 371 (c)(1),
(2) Date: Mar. 4, 2016

(87) PCT Pub. No.: WO2015/035148
PCT Pub. Date: Mar. 12, 2015

(65) Prior Publication Data
US 2016/0216241 A1    Jul. 28, 2016

Related U.S. Application Data

(60) Provisional application No. 61/874,706, filed on Sep. 6, 2013, provisional application No. 61/933,294, filed on Jan. 29, 2014.

(51) Int. Cl.
*G01N 7/00* (2006.01)
*G01N 30/96* (2006.01)
(Continued)

(52) U.S. Cl.
CPC ......... *G01N 30/96* (2013.01); *G01N 1/2205* (2013.01); *G01N 1/2214* (2013.01); *G01N 1/405* (2013.01); *G01N 2030/025* (2013.01)

(58) Field of Classification Search
CPC ...... G01N 1/22; G01N 1/2202; G01N 1/2205; G01N 1/2214; G01N 30/90; G01N 30/92; G01N 30/96; G01N 2030/025
(Continued)

(56) References Cited

U.S. PATENT DOCUMENTS 3,985,017 A    10/1976    Goldsmith
D320,842 S    10/1991    Roman
(Continued)

FOREIGN PATENT DOCUMENTS

JP    2003 222577 A    8/2003
WO    WO 2005/057177 A1    6/2005
WO    WO 2008/015031 A1    2/2008

OTHER PUBLICATIONS

2012 Parts Catalog Ordering Information Terms and Conditions, Dec. 31, 2012, http://www.urgcorp.com/lobrary/catalogs/URG%20cATALOG%202012.pdf.
(Continued)

*Primary Examiner* — Benjamin Schmitt
(74) *Attorney, Agent, or Firm* — Entegris, Inc.

(57) ABSTRACT

Described herein are liquid-free traps for trace levels of an acidic or basic airborne molecular contaminant in a gas. In one version of the invention described herein, the liquid-free trap comprises a housing, comprising an inlet and an outlet; a flow path between the inlet and the outlet; and a rigid sintered hydrophilic material situated in the flow path between the inlet and the outlet and sealed in the housing. The rigid sintered hydrophilic material is functionalized with from about 0.05 molar milliequivalents to about 10
(Continued)

molar milliequivalents of a basic species for trapping an acidic airborne molecular contaminant in the gas or from about 0.05 molar milliequivalents to about 10 molar milliequivalents of an acidic species for trapping a basic airborne molecular contaminant in the gas. Methods of using the liquid-free traps to detect or measure trace levels of an acidic or basic airborne molecular contaminant are also described.

22 Claims, 11 Drawing Sheets

(51) Int. Cl.
G01N 1/22 (2006.01)
G01N 1/40 (2006.01)
G01N 30/02 (2006.01)

(58) Field of Classification Search
USPC .............. 73/23.4, 23.41, 31.03, 31.05, 31.07
See application file for complete search history.

(56) References Cited

U.S. PATENT DOCUMENTS

| | | | |
|---|---|---|---|
| 5,302,191 A | | 4/1994 | Koutrakis |
| 5,438,884 A | * | 8/1995 | Suddath .................. G01N 1/22 73/864.62 |
| 5,759,405 A | * | 6/1998 | Anderson, Jr. .... B01D 15/3885 210/198.2 |
| D473,633 S | | 4/2003 | Chun-Lee |
| D543,948 S | | 6/2007 | Montena |
| 7,430,893 B2 | | 10/2008 | Grafer et al. |

OTHER PUBLICATIONS

CollectTorr, Microcontamination Inspection Service, 2pgs. (2009).
Dean, K. R., et al., (1997). "Effects of Airborne Molecular Contamination on DUV Photoresists", Journal of Photopolymer Science and Technology, 10(3), 425-443.
Giguère, P.A., et al., (1980). "The nature of hydrofluoric acid. A spectroscopic study of the proton-transfer complex H3O+. . . F–". Journal of the American Chemistry Society 102 (17): 5473.
Grenon B., Bhattacharyya K., Volk W., Phan K., Poock A., "Reticle surface contaminants and their relationship to sub-pellicle defect formation", Proceedings of SPIE, Metrology, Inspection and Process control for Microlithography XVIII, vol. 5375, pp. 355-362, (2004).
Gutherie, P. "Tautomeric equilibria and pKa values for 'sulfurous acid' in aqueous solution: a thermodynamic analysis", Canadian Journal of Chemistry, 57, pp. 454 (1979).
Hatakeyama, H., et al., "Interaction between water and hydrophilic polymers," Thermochimica acta 308.1 (1998): 3-22.
Inagaki, N., et al. "Hydrophilic surface modification of polyethylene by plasma exposure," Polymer Preprints 31.2 (1990): 380-381.
International Roadmap Committee (IRC), ITRS Yield Enhancement Table, Table YE4 "AMC Monitoring Methods" (2012).
Korsmeyer, R.W., et al. "Mechanisms of solute release from porous hydrophilic polymers," International Journal of Pharmaceutics 15.1 (1983): 25-35.
Lobert, J., et al., "Virtual NOx-: A Measurement Artifact in Wet Impinger Air Sampling.", Entegris Application Note APN000015, (2006).
Notification Concerning Transmittal of International Preliminary Report on Patentability for International Application No. PCT/US2014/054266, "Liquid-Free Sample Traps and Analytical Method for Measuring Trace Level Acidic and Basic AMC"; dated Mar. 17, 2016.
Notification of Transmittal of the International Search Report and the Written Opinion of the International Searching Authority, or the Declaration for International Application No. PCT/US2014/054266, "Liquid-Free Sample Traps and Analytical Method for Measuring Trace Level Acidic and Basic AMC"; dated Apr. 7, 2015.
Search Report for Taiwan Application No. 103307311, "Liquid-Free Trap for Trace Level Acidic and Basic AMC and Components Thereof", date of completion: Jul. 9, 2015.
Search Report for Taiwan Application No. 104305936, "Liquid-Free Trap for Trace Level Acidic and Basic AMC and Components Thereof", date of completion: Jan. 5, 2016.
Sutton, M.A., et al., (2001) A new diffusion denuder system for long-term, regional monitoring or atmospheric ammonia and ammonium, Water, Air and Soil Pollution: Focus, 1, 145-146.
Vogt, S., et al., "Monitoring acidic and basic contamination in leading edge lithography and metrology applications: quantative comparison of solid-state and impinger based sampling methods.", Proceedings of SPIE, Metrology, Inspection and Process Control for Microlithography XXIV, vol. 7638, pp. 7638, 763825-7, (2010).

* cited by examiner

LIQUID-FREE SAMPLE TRAPS AND ANALYTICAL METHOD FOR MEASURING TRACE LEVEL ACIDIC AND BASIC AMC

RELATED APPLICATIONS

This application is the U.S. National Stage of International Application No. PCT/US2014/054266, filed Sep. 5, 2014, which designates the U.S., published in English, and claims the benefit of U.S. Provisional Application No. 61/874,706, filed Sep. 6, 2013, and U.S. Provisional Application No. 61/933,294, filed on Jan. 29, 2014. The entire teachings of the above applications are incorporated herein by reference.

BACKGROUND OF THE INVENTION

The measurement of parts-per-trillion level acidic and basic airborne molecular contamination (AMC) is essential for process protection and yield control in semiconductor photolithography and adjacent applications. Real-time monitoring solutions are highly desired, as they provide instantaneous and continuous measurement. However, even the most advanced monitors cannot achieve detection limits in the low parts-per-trillion range, and many restrictions apply for the detection of acidic AMC.

Discontinuous sampling with sample traps is capable of achieving parts-per-trillion level measurement, but the currently accepted methods use sample traps filled with deionized water (also commonly referred to as impingers, bubblers and beakers, and all of which are referred to herein as impingers) to capture soluble acidic and basic AMC. Several inherent disadvantages of these methods result in inconsistent data and increased detection limits. Some proprietary solid state solutions have been reported, but involve complex preparation, have high background signals and require 24-72 hour sample duration, or they are protected trade secrets that are not available as an industry standard.

Thus, there is a need for a sample trap and analytical method for measuring trace level acidic and basic airborne molecular contaminants, particularly those acidic and basic airborne molecular contaminants typically encountered in the semiconductor industry, that overcomes these disadvantages, has a low (e.g., parts-per-quadrillion) detection limit and requires a shorter (e.g., 4-8 hour) sample time.

SUMMARY OF THE INVENTION

Described herein is a liquid-free sample trap that allows parts-per-quadrillion (ppq) measurement of acidic and basic AMC, for example, in a gas stream from a cleanroom or other semiconductor manufacturing facility, within a shorter (e.g., 4-6 hour) sampling period. The liquid-free sample traps described herein can be used in an analytical method to measure trace levels of acidic and basic AMC.

One version of the invention provides a liquid-free trap for trace levels of an acidic or basic airborne molecular contaminant in a gas. The liquid-free trap comprises a housing, comprising an inlet and an outlet; a flow path between the inlet and the outlet; and a rigid sintered hydrophilic material situated in the flow path between the inlet and the outlet and sealed in the housing. The rigid sintered hydrophilic material is functionalized with from about 0.05 molar milliequivalents to about 10 molar milliequivalents of a basic species for trapping an acidic airborne molecular contaminant in the gas or from about 0.05 molar milliequivalents to about 10 molar milliequivalents of an acidic species for trapping a basic airborne molecular contaminant in the gas.

Another version of the invention is a liquid-free trap for trace levels of an acidic or basic airborne molecular contaminant in a gas, comprising a housing, comprising an inlet and an outlet; a flow path between the inlet and the outlet; and a rigid sintered hydrophilic material situated in the flow path between the inlet and the outlet and sealed in the housing. The rigid sintered hydrophilic material is functionalized with from about 0.05 molar milliequivalents to about 10 molar milliequivalents of a basic species that forms a solvent soluble (e.g., water-soluble) reaction product with an acidic airborne molecular contaminant in the gas or from about 0.05 molar milliequivalents to about 10 molar milliequivalents of an acidic species that forms a solvent soluble (e.g., water-soluble) reaction product with a basic airborne molecular contaminant in the gas.

Another version of the invention is a liquid-free trap for trace levels of a basic airborne molecular contaminant in a gas. The liquid-free trap comprises a housing, comprising an inlet and an outlet; a flow path between the inlet and the outlet; and a rigid sintered hydrophilic material situated in the flow path between the inlet and the outlet and sealed in the housing. The rigid sintered hydrophilic material is hydrophilic ultrahigh molecular weight polyethylene having an average pore size of from about 5 microns to about 50 microns and is functionalized with phosphoric acid.

Yet another version of the invention is a liquid-free trap for trace levels of an acidic airborne molecular contaminant in a gas. The liquid-free trap comprises a housing, comprising an inlet and an outlet; a flow path between the inlet and the outlet; and a rigid sintered hydrophilic material situated in the flow path between the inlet and the outlet and sealed in the housing. The rigid sintered hydrophilic material is sintered stainless steel having an average pore size of from about 5 microns to about 50 microns and is functionalized with an alkali metal carbonate or bicarbonate (e.g., sodium carbonate).

Another version of the invention is a method for trapping trace levels of an acidic or basic airborne molecular contaminant in a gas stream. The method comprises passing a gas stream into the inlet through the flow path and out of the outlet of a liquid-free trap described herein at a flow rate and for a period of time sufficient to trap a detectable quantity of the acidic or basic airborne molecular contaminant with the rigid sintered hydrophilic material.

Another version of the invention is a method for detecting or measuring trace levels of an acidic or basic airborne molecular contaminant in a gas stream. The method comprises providing a liquid-free trap for trace levels of an acidic or basic airborne molecular contaminant; passing a gas stream into the inlet through the flow path and out of the outlet of the liquid-free trap at a flow rate and for a period of time sufficient to trap a detectable quantity of the acidic or basic airborne molecular contaminant with the rigid sintered hydrophilic material; desorbing the trapped acidic or basic airborne molecular contaminant from the rigid sintered hydrophilic material, thereby providing a sample; and analyzing the sample for trace levels of the acidic or basic airborne molecular contaminant, thereby measuring trace levels of an acidic or basic airborne molecular contaminant in a gas stream. The liquid-free trap comprises a housing, comprising an inlet and an outlet; a flow path between the inlet and the outlet; and a rigid sintered hydrophilic material sealed in the housing between the inlet and the outlet. The rigid sintered hydrophilic material is functionalized with from about 0.05 molar milliequivalents to about 10 molar milliequivalents of a basic species for trapping an acidic airborne molecular contaminant or from about 0.05 molar milliequivalents to about 10 molar milliequivalents of an acidic species for trapping a basic airborne molecular contaminant.

Another version of the invention is a housing for a liquid-free trap for trace levels of an acidic or basic airborne molecular contaminant in a gas. The housing comprises a hollow, substantially cylindrical upstream component having a longitudinal axis and comprising an inner surface, an outer surface, an inlet and an upstream surface, the inner surface having a tapered portion tapering outwardly from the inlet to the upstream surface and terminating at the upstream surface; a hollow, substantially cylindrical downstream component comprising an outlet and a downstream surface; and a locking nut to secure the upstream component to the downstream component without causing the upstream and downstream components to rotate with respect to one another. The upstream surface and the downstream surface together create a space that is sealed from the environment and situated in a flow path between the inlet and the outlet.

The liquid-free traps described herein and the methods for measuring trace levels of an acidic or basic airborne molecular contaminant in a gas stream using the liquid-free traps described herein allow ppq level measurement of acidic and basic AMC within one work shift, typically, a 4-6 hour sample period. The traps can easily be manufactured and prepared in small lab operations, are sealed from external contamination, including contamination due to operator handling in the field, have months of shelf life and show high capture efficiencies while minimizing secondary chemical reactions and analytical artifacts. Capacity results for the liquid-free base trap using ammonia ($NH_3$) as a test gas yielded more than 200 parts-per-billion-hour (ppb-h) at 100% capture efficiency without any moisture (simulating sampling of clean dry air (CDA) or $N_2$) and 350 ppb-h at 40% relative humidity (RH). Given modern supply gas concentrations of ammonia of less than 1 ppb, and cleanroom concentrations of less than 10 ppbV ammonia, the capture efficiencies achieved for ammonia translate to a quantitative capture of ammonia for 20-35 hours of sampling at 3.5 liters per minute (lpm), much in excess of what is required for ppq level analysis. This allows for the sampling of AMC within one work shift and without the need for overnight (typically, 12-72 hours) sampling, enabling quicker and more accurate identification of the potential source(s) of AMC.

Performance testing indicates that the liquid-free traps described herein provide more precise and more accurate results for $NH_3$, $SO_2$ and HF in comparison to standard impingers in lab testing, with a relative standard deviation not exceeding 8% and capture efficiency greater than 95% for all three compounds. Acetic acid was the only compound that showed slightly decreased performance but still maintained a precision and accuracy comparable to the other compounds tested. In-field validation deployment of the liquid-free traps described herein to external and internal customers in parallel with standard wet impingers resulted in less than 10% difference between the traps, providing evidence that the liquid-free traps are suitable for replacement of wet impingers in the field.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1A:
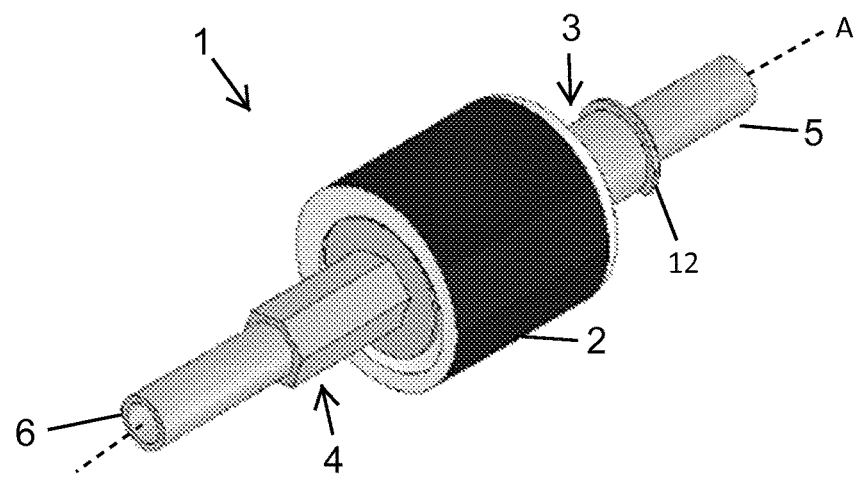
FIG. 1A is a representation of a liquid-free trap housing in one version of the invention.

A description of example embodiments of the invention follows.

As used herein, the singular forms "a", "an" and "the" include plural referents unless the context clearly dictates otherwise. Thus, for example, reference to "an airborne molecular contaminant" can include a plurality of airborne molecular contaminants. Further, the plurality can comprise more than one of the same airborne molecular contaminants or a plurality of different airborne molecular contaminants.

Unless defined otherwise, all technical and scientific terms used herein have the same meanings as commonly understood by one of ordinary skill in the art. Methods and materials similar or equivalent to those described herein can be used in the practice or testing of embodiments of the present invention. Nothing herein is to be construed as an admission that the invention is not entitled to antedate such disclosure by virtue of prior invention. "Optional" or "optionally" means that the subsequently described event or circumstance may or may not occur, and that the description includes instances where the event occurs and instances where it does not. All numeric values herein can be modified by the term "about," whether or not explicitly indicated. The term "about" generally refers to a range of numbers that one of skill in the art would consider equivalent to the recited value (i.e., having the same function or result). In some embodiments, the term "about" refers to ±10% of the stated value, in other embodiments, the term "about" refers to +2% of the stated value. While compositions and methods are described in terms of "comprising" various components or steps (interpreted as meaning "including, but not limited to"), the compositions and methods can also "consist essentially of" or "consist of" the various components and steps, such terminology should be interpreted as defining essentially closed or closed member groups.

Although the invention is shown and described with respect to one or more implementations, equivalent alterations and modifications will occur to others skilled in the art based upon a reading and understanding of this specification. In addition, while a particular feature or aspect of the invention may have been disclosed with respect to only one of several implementations, such feature or aspect may be combined with one or more other features or aspects of the other implementations as may be desired and advantageous for any given or particular application. Furthermore, to the extent that the terms "includes", "having", "has", "with", or variants thereof, are used in either the detailed description or the claims, such terms are intended to be inclusive in a manner similar to the term "comprising." Also, the term "exemplary" is merely meant to mean an example, rather than the best. It is also to be appreciated that features, layers and/or elements depicted herein are illustrated with particular dimensions and/or orientations relative to one another for purposes of simplicity and ease of understanding, and that the actual dimensions and/or orientations may differ substantially from that illustrated herein.

Liquid-Free Traps

One version of the invention provides a liquid-free trap for trace levels of an acidic or basic airborne molecular contaminant in a gas. The liquid-free trap comprises a housing, comprising an inlet and an outlet; a flow path between the inlet and the outlet; and a rigid sintered hydrophilic material situated in the flow path between the inlet and the outlet and sealed in the housing. The rigid sintered hydrophilic material is functionalized with from about 0.05 molar milliequivalents to about 10 molar milliequivalents of a basic species for trapping an acidic airborne molecular contaminant in the gas or from about 0.05 molar milliequivalents to about 10 molar milliequivalents of an acidic species for trapping a basic airborne molecular contaminant in the gas.

Another version of the invention is a liquid-free trap for trace levels of an acidic or basic airborne molecular contaminant in a gas, comprising a housing, comprising an inlet and an outlet; a flow path between the inlet and the outlet; and a rigid sintered hydrophilic material situated in the flow path between the inlet and the outlet and sealed in the housing. The rigid sintered hydrophilic material is functionalized with from about 0.05 molar milliequivalents to about 10 molar milliequivalents of a basic species that forms a solvent soluble (e.g., water-soluble) reaction product with an acidic airborne molecular contaminant in the gas or from about 0.05 molar milliequivalents to about 10 molar milliequivalents of an acidic species that forms a solvent soluble (e.g., water-soluble) reaction product with a basic airborne molecular contaminant in the gas. Exemplary solvents are described hereinbelow. In more particular versions of the invention, the reaction product is insoluble in the gas (a solvent-soluble, gas-insoluble reaction product).

The gas can be gas from a cleanroom, electrochemical deposition, chemical mechanical planarization (CMP), wafer handling or dry etch, or any inert supply gas, such as, but not limited to, argon, nitrogen, clean dry air (CDA) or EXTREME CLEAN DRY AIR (XCDA®, available from Entegris, Inc.).

"Liquid-free trap," as used herein, refers to a trap that relies on a solid material (e.g., a rigid sintered hydrophilic material), rather than a liquid, to trap an AMC. Liquid-free traps are distinguishable from standard impingers, for example, which rely on liquid, typically, water, to trap AMC.

It is to be understood that the liquid-free traps disclosed herein can be used to trap a single acidic or basic airborne molecular contaminant or a plurality (e.g., more than one, two, three, four, five, etc.) of acidic or basic airborne molecular contaminants. Further, the plurality can comprise more than one of the same airborne molecular contaminants or a plurality of different airborne molecular contaminants (e.g., more than one, two, three, four, five, etc.).

"Trace levels," as used herein, refers to a concentration of an acidic or basic AMC of less than 1 part-per-million. Typically, trace levels refer to concentrations in the parts-per-quadrillion (ppq), parts-per-trillion (ppt) and parts-per-billion (ppb) ranges.

"Airborne molecular contaminant," as used herein, refers to chemical contaminants, typically in the form of vapors, that can have a detrimental effect on a product or process, particularly in the semiconductor industry and adjacent industries. Exemplary airborne molecular contaminants include, but are not limited to, salts of Group I and Group II metals, hydrogen halides (e.g., HF, HCl), $SO_2$, $SO_x$ wherein x is 1 or 2, $NO_x$ wherein x is 1 or 2, siloxanes, organophosphorus compounds, amines (e.g., water-soluble primary, secondary and tertiary amines, ammonia), moisture, oxygen, hydrocarbons (typically, having fewer than 30 carbon atoms), organic water-soluble acids, inorganic oxyacids (e.g., those oxyacids with a primary pKa of less than 4.76, sulfuric acid, nitric acid, nitrous acid, phosphoric acid), volatile acids and bases.

As used herein, "acidic airborne molecular contaminant" refers to airborne molecular contaminants that will undergo an acid-base reaction with a base. For example, hydrogen fluoride chemically reacts with sodium bicarbonate in an acid-base reaction to form sodium fluoride, carbon dioxide gas and water (see Exemplification, Equation (11)). Exemplary acidic airborne molecular contaminants include hydrogen halide (e.g., HF, HCl), chlorine, nitrogen dioxide, nitric oxide, sulfur dioxide, organic water-soluble acids (e.g., acetic acid) and inorganic oxyacids (e.g., those oxyacids with a primary pKa of less than 4.76, sulfuric acid, nitric acid, nitrous acid, phosphoric acid).

In some versions of the liquid-free traps described herein, the acidic airborne molecular contaminant is a hydrogen halide (e.g., HF, HCl), an organic water-soluble acid (e.g., acetic acid) or an inorganic oxyacid (e.g., those oxyacids with a primary pKa of less than 4.76, sulfuric acid, nitric acid, nitrous acid, phosphoric acid). In some versions of the liquid-free traps described herein, the acidic AMC is sulfur dioxide, a hydrogen halide (e.g., HF, HCl) or a water-soluble organic acid (e.g., acetic acid), or a combination of the foregoing.

As used herein, "basic airborne molecular contaminant" refers to airborne molecular contaminants that will undergo an acid-base reaction with an acid. For example, ammonia chemically reacts with phosphoric acid to form ammonium dihydrogen phosphate and diammonium monohydrogen phosphate (see Exemplification, Equation (4)). Exemplary basic airborne molecular contaminants include amines (e.g., water-soluble primary, secondary and tertiary amines, ammonia).

In some versions of the liquid-free traps described herein, the basic airborne molecular contaminant is an amine (e.g., a primary, secondary or tertiary water-soluble amine, ammonia, preferably ammonia).

"Rigid," used herein in reference to a rigid sintered hydrophilic material, refers to a material that maintains its structural integrity (e.g., does not rupture or significantly distort or consist of a granular form, is able to form and maintain an integral seal with the housing) under vacuum or at pressures up to about 10 atm or at flow rates of a gas stream of up to about 20 liters per minute (lpm). It will be understood that rigidity is often a function of the thickness of a material. Thus, a rigid material should be adequately thick to maintain its structural integrity under vacuum or at pressures up to about 10 atm or at flow rates of a gas stream of up to about 20 lpm.

In versions of the invention, the rigid sintered hydrophilic material has a thickness of from about 0.025 centimeters to about 2.5 centimeters, from about 0.1 centimeters to about 1.3 centimeters, from about 0.1 centimeters to about 0.65 centimeters, from about 0.25 centimeters to about 0.65 inches, of about 0.3 centimeters or of about 0.15 centimeters.

"Sintered," used herein in reference to a rigid sintered hydrophilic material, refers to a porous solid mass of material. The rigid sintered hydrophilic material can be in the form of a frit or disc. A liquid-free trap can include multiple layers (e.g., one, two, three) of the rigid sintered hydrophilic material. The layers can be the same (e.g., each sintered stainless steel functionalized with sodium carbonate) or different (e.g., sintered stainless steel functionalized with sodium carbonate and sintered stainless steel functionalized with sodium bicarbonate, sintered stainless steel functionalized with sodium carbonate and sintered hydrophilic polyethylene functionalized with phosphoric acid).

In versions of the invention, the rigid sintered hydrophilic material has an average pore size of from about 1 micron to about 100 microns, from about 2 microns to about 50 microns, from about 5 microns to about 50 microns, from about 60 microns to about 90 microns or about 20 microns, although other smaller and larger pore sizes can also be used. Methods for measuring average pore size are well-known in the art. See, for example, ASTM E128-99(2011).

"Hydrophilic," used herein in reference to a rigid sintered hydrophilic material, refers to a material that is wettable with water. In preferred aspects of the invention, a hydrophilic material (e.g., a hydrophilic polymeric material, such as surface-modified ultrahigh molecular weight polyethylene, or stainless steel, such as 316L stainless steel) can have a contact angle of about zero (e.g., 0-10°, 0-5°) with water. A material that is wettable with water can have a surface tension similar to that of water. The surface tension of water is 71.97 dynes/cm at 20° C. Although not wishing to be bound by any particular theory, it is believed that water wets sintered stainless steel by capillary action.

In versions of the invention, the rigid sintered hydrophilic material is sintered metal, such as sintered stainless steel (e.g., type 316L stainless steel).

In some versions of the invention, the rigid sintered hydrophilic material is polymeric, for example, sintered hydrophilic polyethylene (e.g., ultrahigh molecular weight polyethylene), sintered hydrophilic polytetrafluoroethylene, sintered hydrophilic polyethersulfone or sintered hydrophilic nylon.

Methods of increasing the water wettability of polymeric materials, for example, reducing the contact angle of the material with water or increasing the surface tension of the neat material, preferably without altering or without substantially altering the bulk properties of the neat material, are well-known in the art. For example, a hydrophilic coating can be applied to the surface(s) of a neat polymeric material, such as polyethylene, or its surface(s) can be treated with plasma, ultraviolet or laser radiation or with an oxidizing solution to increase the surface energy of the neat polymer and render the material hydrophilic. See, for example, Inagaki, N., et al. "Hydrophilic surface modification of polyethylene by plasma exposure," *Polymer Preprints* 31.2 (1990): 380-381; Korsmeyer, Richard W., et al. "Mechanisms of solute release from porous hydrophilic polymers," *International Journal of Pharmaceutics* 15.1 (1983): 25-35; Hatakeyama, Hyoe and Tatsuko Hatakeyama, "Interaction between water and hydrophilic polymers," *Thermochimica acta* 308.1 (1998): 3-22. Hydrophilic polymeric materials are also commercially available, for example, from GENPORE®, Reading, Pa.

The rigid sintered hydrophilic materials disclosed herein are preferably chemically inert and chemically clean.

Used herein, "chemically clean" refers to a material, for example, a rigid sintered hydrophilic material or a housing, that, upon desorption (e.g., extraction) and analysis, for example, by ion chromatography, produces a signal having an intensity of less than 10% of the detection limit to be achieved for each airborne molecular contaminant with a sampling time of 6 hours. For example, if the detection limit of ammonia to be achieved over a 6-hour sampling time is 10 ppt, a chemically clean material, upon desorption and analysis, will not produce an ammonia signal corresponding to greater than 1 ppt ammonia.

The rigid sintered hydrophilic materials in the liquid-free traps described herein are functionalized with from about 0.05 molar milliequivalents to about 10 molar milliequivalents, from about 0.05 molar milliequivalents to about 5 molar milliequivalents, from about 0.1 molar milliequivalents to about 10 molar milliequivalents, from about 0.1 molar milliequivalents to about 5 molar milliequivalents, from about 1 molar milliequivalent to about 10 molar milliequivalents or about 5 milliequivalents of a basic species for trapping an acidic airborne molecular contaminant in a gas or from about 0.05 molar milliequivalents to about 10 molar milliequivalents, from about 0.05 molar milliequivalents to about 5 molar milliequivalents, from about 0.1 molar milliequivalents to about 10 molar milliequivalents, from about 0.1 molar milliequivalents to about 5 molar milliequivalents, from about 1 molar milliequivalent to about 10 molar milliequivalents or about 5 milliequivalents of an acidic species for trapping a basic airborne molecular contaminant in a gas. The number of molar milliequivalents of the acidic or basic species can be calculated from the capacity of a liquid-free trap, taking into account the identity of the acidic or basic species on the rigid sintered hydrophilic material and the identity of the basic or acidic airborne molecular contaminant.

The basic species is not particularly limited, but should undergo an acid-base reaction with one or more acidic airborne molecular contaminants of interest in a gas to provide a reaction product. Typically, the reaction product is insoluble in the gas such that it precipitates out of the gas and forms a solid salt on the rigid sintered hydrophilic material. In addition, in versions of the invention in which the rigid porous hydrophilic material is intended to be extracted using a solvent, the product of the reaction between the basic species and the acidic airborne molecular contaminant should be soluble in the solvent.

The acidic species is not particularly limited, but should undergo an acid-base reaction with one or more basic airborne molecular contaminants of interest in a gas to provide a reaction product. Typically, the reaction product is insoluble in the gas such that it precipitates out of the gas and forms a solid salt on the rigid sintered hydrophilic material. In versions of the invention in which the rigid porous hydrophilic material is intended to be extracted using a solvent, the product of the reaction between the acidic species and the basic airborne molecular contaminant should be soluble in the solvent. Exemplary solvents are described hereinbelow.

"Functionalized," as used herein, refers to the noncovalent attachment of basic or acidic species to a rigid sintered hydrophilic material, as might be achieved, for example, by surface adsorption. For example, a rigid sintered hydrophilic material can be treated with a weak triprotic acid solution, then dried. Although not wishing to be bound by any particular theory, it is thought that this process causes the acid to crystallize on the surface of the rigid sintered hydrophilic material within the pore structure. A rigid sintered hydrophilic material can also be treated with a solution of base, then dried. Although not wishing to be bound by any particular theory, it is thought that this process causes the base to crystallize on the surface of the rigid sintered hydrophilic material within the pore structure.

In some versions of the invention, the rigid sintered hydrophilic material is functionalized with a basic species. The basic species can be selected from an alkali or alkaline earth metal salt of bicarbonate, carbonate or hydroxide, or a combination of the foregoing (e.g., $NaHCO_3$, $Na_2CO_3$, KOH, etc.). In more specific versions of the invention, the rigid sintered hydrophilic material is functionalized with an alkali earth metal salt of a bicarbonate (e.g., $NaHCO_3$) or carbonate (e.g., $Na_2CO_3$).

In other versions of the invention, the rigid sintered hydrophilic material is functionalized with an acidic species. The acidic species can be a polyprotic acid, for example, phosphoric acid or citric acid, preferably phosphoric acid.

In some versions of the invention, the housing is a polymeric material, for example, acrylonitrilebutadienestyrene (ABS), acrylonitrile ethylene styrene (AES), acrylate styrene acrylonitrile (ASA), cellulose acetate (CA), cellulose acetate butyrate (CAB), ethylenevinylacetate (EVA), high density polyethylene (HDPE), high impact polystyrene (HIPS), liquid crystal polymer (LCP), medium density polystyrene (MDPE), methyl methacrylate(acrylic) (MMA), perfluoroalkoxy, polyarylsulfone, polybutylene terephthalate (PBT), polycarbonate (PC), polyalkoxysulfone, polyamide (PA), polyethylene (PE), polyether ether ketone (PEEK), polyetherketone (PEK), polyetherimide (PEI), polyethersulfone (PES), polyethylene terephthalate (PET), polyoxymethylene (acetal) (POM), polypropylene (PP), polyphthalamide (PPA), polyphenylene oxide (PPO), polyphenylenesulfide (PPS), polystyrene (PS), polysulfone (PSU), polyvinylchloride (PVC), polyvinylidene fluoride (PVDF), styrene acrylonitrile (SAN), thermoplastic elastomer (TPE), thermoplastic olefins (TPO), thermoplastic polyurethane (TPU), ultrahigh molecular weight polyethylene, or blends thereof. Preferred materials for the housing include PEEK and ultrahigh molecular weight polyethylene. A particularly preferred material for the housing is PEEK.

In some versions of the invention, the housing is chemically clean, as that term is described hereinabove.

In some versions of the invention, the housing further comprises an upstream component including the inlet, a downstream component including the outlet and a locking nut to secure the upstream component to the downstream component. A housing according to these versions of the invention is depicted in FIG. 1A. Housing 1 in FIG. 1A is a three-piece housing comprising locking nut 2, upstream component 3 and downstream component 4. Locking nut 2 secures upstream component 3 to downstream component 4. Spring ring 12 prevents locking nut 2 from moving past it. Housing 1 is designed such that upstream component 3 and downstream component 4 do not rotate with respect to one another during assembly or disassembly of the liquid-free trap. FIG. 1A also depicts longitudinal axis A of the upstream and downstream components and the locking nut of housing 1. Although not shown, locking nut 2 can have a knurled, or otherwise textured surface to facilitate assembly and disassembly of the liquid-free trap. Locking nut 2 is also depicted in FIG. 1D.

Upstream component 3 and downstream component 4 each have tube ends, 5 and 6, respectively, that can be used for installing the housing in a manifold, for example. It will be understood that tube ends 5 and 6 can be replaced with any other connection known in the art, for example, a flange. International Publication No. WO 2005/057177, in particular FIG. 5A and description thereof, illustrates a manifold into which a liquid-free trap described herein could be installed for sampling gas from a cleanroom or other semiconductor manufacturing facility, for example.

FIG. 1B is an exploded view of a liquid-free trap assembly in one aspect of the invention. FIG. 1B shows that, in one aspect of the invention, upstream component 3 can have tapered portion 11. In the aspect of the invention depicted in FIG. 1B, tapered portion 11 forms a frustoconical shape and tapers outwardly to upstream surface 14, dimensioned to match or substantially match the dimension(s) (e.g., diameter) of rigid sintered hydrophilic material 7. The tapered portion serves to decrease the velocity of the gas flow and increase the time in which the gas is in contact with the rigid sintered hydrophilic material, thereby increasing the removal efficiency of the liquid-free trap. The angle of the tapered portion, measured from the longitudinal axis A (depicted in FIG. 1A) of the upstream component, is from about 5° to about 45°, from about 10° to about 30° or about 15°. Upstream component 3 also has a stop in the form of flange 17. Groove 9 on upstream component 3 provides a groove in which spring ring 12 (not depicted) resides. In preferred versions of the invention, the upstream component is fabricated as a unitary element. Upstream component 3 is also depicted in FIG. 1E.

Downstream component 4 is depicted in FIG. 1F. In FIG. 1F, downstream component 4 has downstream seat 13, also dimensioned to match or substantially match the dimensions of rigid sintered hydrophilic material 7. Threads 15 on downstream component 4 mate with threads 16 on locking nut 2 to secure upstream component 3 to downstream component 4. Although not required, hex nut 10 provides downstream component 4 with a grip that can be particularly useful in loosening locking nut 2 after use of the liquid-free trap. Hex nut 10 also provides a grip that is useful in sealing the liquid-free trap. Hex nut 10 can be any shape that provides a grip to facilitate sealing and unsealing locking nut 2. In preferred versions of the invention, downstream component 4 is fabricated as a unitary element.

Rigid sintered hydrophilic material 7 is sealed, in the version of the invention depicted in FIGS. 1B and 1D-1G, between upstream surface 14 of upstream component 3 and downstream seat 13 of downstream component 4 by pressure created by tightening locking nut 2. Together, upstream surface 14 and downstream seat 13 seal rigid sintered hydrophilic material 7 from outside exposure or contamination while maintaining a flow path between tube end or inlet 5 and tube end or outlet 6. See FIG. 1G. As can be seen in FIG. 1G, even in the sealed and assembled positioned, flange 17 stops a portion of upstream component 3 from entering threads 16 of locking nut 2 and creates a gap between flange 17 of upstream component 3 and downstream component 4. The gap serves to ensure there is adequate distance over which locking nut 2 can be tightened to seal the rigid sintered hydrophilic material in the housing. Rigid sintered hydrophilic material 7 can also be sealed between upstream component 3 and downstream component 4 using o-rings 8, depicted in FIG. 1C. Housing 1 secures the rigid sintered hydrophilic material without twisting or tearing of the rigid sintered hydrophilic material.

A particular version of the invention is a liquid-free trap for trace levels of a basic airborne molecular contaminant in a gas. The liquid-free trap comprises a housing, comprising an inlet and an outlet; a flow path between the inlet and the outlet; and a rigid sintered hydrophilic material situated in the flow path between the inlet and the outlet and sealed in the housing. The rigid sintered hydrophilic material is hydrophilic ultrahigh molecular weight polyethylene having an average pore size of from about 5 microns to about 50 microns and is functionalized with phosphoric acid. In a particular aspect of this version of the invention, the basic airborne molecular contaminant is an amine (e.g., a water-soluble primary, secondary or tertiary amine, ammonia, preferably ammonia). In another particular aspect of this version of the invention, the rigid sintered hydrophilic material is functionalized with from about 1 to about 10 and, preferably, about 5, molar milliequivalents of phosphoric acid.

Another particular version of the invention is a liquid-free trap for trace levels of an acidic airborne molecular contaminant in a gas. The liquid-free trap comprises a housing, comprising an inlet and an outlet; a flow path between the inlet and the outlet; and a rigid sintered hydrophilic material situated in the flow path between the inlet and the outlet and sealed in the housing. The rigid sintered hydrophilic material is sintered stainless steel having an average pore size of from about 5 microns to about 50 microns and is functionalized with an alkali metal carbonate (e.g., sodium carbonate) or bicarbonate (e.g., sodium bicarbonate). In a particular aspect of this version of the invention, the rigid sintered hydrophilic material is functionalized with from about 1 to about 10 and, preferably, about 5, molar milliequivalents of the alkali metal carbonate or bicarbonate. In another particular aspect of this version of the invention, the acidic airborne molecular contaminant is an oxyacid (e.g., sulfuric acid, nitric acid, nitrous acid, phosphoric acid), sulfur dioxide, a hydrogen halide (e.g., HF, HCl) or a water-soluble organic acid (e.g., acetic acid), or a combination of the foregoing. In yet another particular aspect of this version of the invention, the acidic airborne molecular contaminant is sulfur dioxide, a hydrogen halide (e.g., HF, HCl) or a water-soluble organic acid (e.g., acetic acid), or a combination of the foregoing.

One version of the invention is a manifold comprising a liquid-free trap for trace levels of an acidic or basic AMC in a gas. In a specific version of the invention, the manifold comprises a liquid-free trap for trace levels of an acidic airborne molecular contaminant and a liquid-free trap for trace levels of a basic airborne molecular contaminant. International Publication No. WO 2005/057177, in particular FIG. 5A and description thereof, illustrates a manifold into which one or more liquid-free traps described herein could be installed. Sample traps for organic AMC (e.g., carbon traps) may also optionally be installed in the manifold. The liquid-free trap for trace levels of an acidic airborne molecular contaminant and the liquid-free trap for trace levels of a basic airborne molecular contaminant can be connected in series or in parallel, preferably in parallel.

Another version of the invention is a system, comprising a liquid-free trap described herein; and a pump or a gas humidifier, or a combination of the foregoing (a pump and a gas humidifier).

Housings

Another version of the invention is a housing for a liquid-free trap for trace levels of an acidic or basic airborne molecular contaminant in a gas. The housing comprises a hollow, substantially cylindrical upstream component having a longitudinal axis and comprising an inner surface, an outer surface, an inlet and an upstream surface, the inner surface having a tapered portion tapering outwardly from the inlet to the upstream surface and terminating at the upstream surface; a hollow, substantially cylindrical downstream component comprising an outlet and a downstream surface; and a locking nut to secure the upstream component to the downstream component without causing the upstream and downstream components to rotate with respect to one another. The upstream surface and the downstream surface together create a space that is sealed from the environment and situated in a flow path between the inlet and the outlet.

Exemplary materials for the upstream component, the downstream component and the locking nut are as described above with respect to housing materials. In preferred versions of the invention, the upstream component, the downstream component and the locking nut are PEEK.

In some versions, the upstream component or the downstream component, preferably, the downstream component, further comprises a grip to facilitate sealing and unsealing of the locking nut.

In some versions, the upstream component or the downstream component, preferably the downstream component, further comprises threads on an exterior surface thereof and the locking nut comprises threads on an interior surface thereof for mating with the threads of the upstream component or the downstream component, preferably the downstream component.

In some versions, the housing (e.g., the upstream component, the downstream component, preferably, the upstream component) further comprises a spring ring for preventing the locking nut from disengaging from the upstream component or the downstream component, preferably the upstream component.

In some versions, the upstream component further comprises a stop for preventing the locking nut from disengaging from the upstream component and to secure the upstream component in the locking nut upon assembly of the housing (see, for example, flange 17 in FIG. 1G). In some versions, a spring ring situated on the upstream component and the stop together prevent the locking nut from disengaging from the upstream component.

In some versions, the tapered portion tapers outwardly at an angle of from about 5° to about 45°, from about 10° to about 30° or about 15° from the longitudinal axis of the upstream component.

It will be understood that any of the housings described herein can be incorporated into the liquid-free traps of the invention by situating a rigid sintered hydrophilic material in the space created by the upstream surface and the downstream surface. Thus, some version provide a liquid-free trap for trace levels of an acidic or basic airborne molecular contaminant in a gas, comprising a housing described herein; and a rigid sintered hydrophilic material situated in the flow path in the space created by the upstream component and the downstream component between the inlet and the outlet and sealed in the housing. Aspects and alternative aspects of the rigid sintered hydrophilic material are as described herein with respect to liquid-free traps.

Methods

Another version of the invention is a method for trapping trace levels of an acidic or basic airborne molecular contaminant in a gas stream. The method comprises passing a gas stream into the inlet through the flow path and out of the outlet of a liquid-free trap described herein at a flow rate and for a period of time sufficient to trap a detectable quantity of the acidic or basic airborne molecular contaminant with the rigid sintered hydrophilic material.

Another version of the invention is a method for detecting or measuring trace levels of an acidic or basic airborne molecular contaminant in a gas stream. The method comprises providing a liquid-free trap for trace levels of an acidic or basic airborne molecular contaminant; passing a gas stream into the inlet through the flow path and out of the outlet of the liquid-free trap at a flow rate and for a period of time sufficient to trap a detectable quantity of the acidic or basic airborne molecular contaminant with the rigid sintered hydrophilic material; desorbing the trapped acidic or basic airborne molecular contaminant from the rigid sintered hydrophilic material, thereby providing a sample; and analyzing the sample for trace levels of the acidic or basic airborne molecular contaminant. The liquid-free trap comprises a housing, comprising an inlet and an outlet; a flow path between the inlet and the outlet; and a rigid sintered hydrophilic material sealed in the housing between the inlet and the outlet. The rigid sintered hydrophilic material is functionalized with from about 0.05 to about 10 molar milliequivalents of a basic species for trapping an acidic airborne molecular contaminant or from about 0.05 to about 5 molar milliequivalents of an acidic species for trapping a basic airborne molecular contaminant. Aspects and alternative aspects of the liquid-free trap are as described above.

It is to be understood that the methods disclosed herein can be used to trap, detect or measure trace levels of a single acidic or basic airborne molecular contaminant or a plurality (e.g., more than one, two, three, four, five, etc.) of acidic or basic airborne molecular contaminants. Further, the plurality can comprise more than one of the same airborne molecular contaminants or a plurality of different airborne molecular contaminants (e.g., more than one, two, three, four, five, etc.).

"Detectable quantity," as used herein, refers to an amount or concentration of trapped airborne molecular contaminant greater than the method detection limit (MDL). The MDL is the minimum amount or concentration of airborne molecular contaminant required to produce a signal that can be considered to be different from zero with 99% statistical confidence. MDL can be determined using the Hubaux-Vos method. Typically, an MDL needs to be in the high ppq range to report low-ppt level AMC.

In some versions of the methods described herein, the period of time is from about 0.5 hours to about 8 hours, from about 2 hours to about 8 hours, from about 4 hours to about 6 hours or about 6 hours.

In some versions of the methods described herein, the flow rate of the gas stream into the inlet through the flow path and out of the outlet of the liquid-free trap is greater than zero and less than about 20 lpm, less than about 10 lpm, less than about 5 lpm or less than about 4 lpm. In some versions the flow rate is about 4 lpm. In some versions, the flow rate is from about 0.5 lpm to about 5 lpm or from about 0.5 to about 4 lpm.

In preferred versions of the invention, desorbing comprises extracting the trapped acidic or basic airborne molecular contaminant from the rigid sintered hydrophilic material using a solvent. The solvent in these versions of the invention is not particularly limited and includes any solvent that does not interfere with the analytical method (e.g., ion chromatography). "Solvent," used herein, is meant to encompass use of either a single solvent or a mixture of solvents in the extraction. Exemplary solvents include organic solvents (e.g., water-miscible organic solvents, such as ethanol, acetone and acetonitrile), water, and mixtures thereof (e.g., a water-miscible organic solvent and water, such as 40% ethanol in water). Ion chromatography compatible organic solvents include solvents, such as ethanol, acetone and acetonitrile, having a surface tension of less than 30 dynes/cm.

In some versions of the invention, the solvent is water or a mixture of a water-miscible organic solvent and water. In preferred versions of the invention, the solvent is water. Water used for extraction should typically be deionized water to prevent contamination of the sample.

The gas stream can be a gas stream from a cleanroom, electrochemical deposition, chemical mechanical planarization (CMP), wafer handling or dry etch, or a stream of any inert supply gas, such as, but not limited to, argon, nitrogen, clean dry air (CDA) or EXTREME CLEAN DRY AIR (XCDA®, available from Entegris, Inc.). XCDA® contains <1 ppb $H_2O$, <10 ppt volatile bases, <1 ppt all other contaminants.

In some versions of the methods described herein, extracting the trapped acidic or basic airborne molecular contaminant using a solvent can comprise ultrasonically treating a mixture of the rigid sintered hydrophilic material and the solvent.

Analysis of the sample can include detection (e.g., identifying the presence or absence of a particular acidic or basic airborne molecular contaminant) and/or calculation of the level (e.g., concentration, amount) of the acidic or basic airborne molecular contaminant in the gas stream. Typically, analyzing the sample includes calculating the level of the acidic or basic airborne molecular contaminant in the gas stream, thereby measuring trace levels of the acidic or basic airborne molecular contaminant in the gas stream. Calculation can be achieved, for example, by quantifying the concentration of the acidic or basic airborne molecular contaminant in the sample and using the sample concentration to calculate the gas-phase concentration of the airborne molecular contaminant by using the flow rate and sample time to determine the overall air or gas volume collected. Quantification of the concentration of the acidic or basic airborne molecular contaminant can be achieved, for example, by comparing to a standard or calibration curve or by using other techniques known in the art.

A wide variety of techniques can be used to analyze the sample, including gas phase chromatography mass spectrometry (GCMS) (e.g., for airborne molecular contaminants desorbed into the gas phase), chemiluminescence (e.g., for ammonia, by catalytic conversion of ammonia into NO, followed by chemiluminescent detection of NO), fluorometry (e.g., by addition of a suitable dye to the sample) and ion chromatography (e.g., for airborne molecular contaminants desorbed into a liquid, such as a solvent). A preferred analytical technique is ion chromatography.

In some versions of the methods described herein, analyzing the sample comprises analyzing the sample using ion chromatography. Ion chromatography is a well-known technique. Specific ion chromatography conditions useful in analyzing the samples described herein can be found in the Exemplification.

In some versions of the invention, the method further comprises removing the rigid sintered hydrophilic material from the housing, for example, prior to desorbing the trapped acidic or basic airborne molecular contaminant from the rigid sintered hydrophilic material.

Another version of the invention is a method for measuring trace levels of an acidic or basic airborne molecular contaminant in a gas stream, comprising providing a manifold comprising a liquid-free trap for trace levels of an acidic or basic airborne molecular contaminant; passing a gas stream into the inlet through the flow path and out of the outlet of the liquid-free trap at a flow rate and for a period of time sufficient to trap a detectable quantity of the acidic or basic airborne molecular contaminant with the rigid sintered hydrophilic material; desorbing the trapped acidic or basic airborne molecular contaminant from the rigid sintered hydrophilic material, thereby providing a sample; and analyzing the sample for trace levels of the acidic or basic airborne molecular contaminant. Aspects and alternative aspects of the liquid-free trap are as described herein. Aspects and alternative aspects of the method are as described above.

In a particular version of the invention, the method comprises providing a manifold comprising a liquid-free trap for trace levels of an acidic airborne molecular contaminant and a liquid-free trap for trace levels of a basic airborne molecular contaminant; passing a gas stream into the inlet through the flow path and out of the outlet of the liquid-free trap for trace levels of an acidic airborne molecular contaminant at a flow rate and for a period of time sufficient to trap a detectable quantity of the acidic airborne molecular contaminant with the rigid sintered hydrophilic material, and passing the gas stream into the inlet through the flow path and out of the outlet of the liquid-free trap for trace levels of a basic airborne molecular contaminant at a flow rate and for a period of time sufficient to trap a detectable quantity of the basic airborne molecular contaminant with the rigid sintered hydrophilic material. The trapped acidic airborne molecular contaminant is desorbed from the rigid sintered hydrophilic material for trapping trace levels of an acidic airborne molecular contaminant, thereby providing a first sample, and the trapped basic airborne molecular contaminant is separately desorbed from the rigid sintered hydrophilic material for trapping trace levels of a basic airborne molecular contaminant, thereby providing a second sample. The first and second samples are separately analyzed for trace levels of the acidic and basic airborne molecular contaminant, thereby measuring trace levels of the acidic and basic airborne molecular contaminant. The liquid-free trap for trace levels of acidic airborne molecular contaminant and the liquid-free trap for trace levels of basic airborne molecular contaminant can be connected in series or in parallel, preferably in parallel.

The liquid-free traps described herein are typically used in an active sampling configuration. As used herein, "active sampling" refers to the use of a gas moving device, such as a pump, coupled to the liquid-free trap to deliver a gas stream to the rigid sintered hydrophilic material. In active sampling, an external source of energy coupled to the liquid-free trap is used to deliver a gas stream to the rigid sintered hydrophilic material. For comparison, passive sampling uses the energy of a gas itself to deliver the gas to the rigid sintered hydrophilic material, such as occurs by diffusion.

In some versions of the methods, a pump is used to draw the gas stream into the inlet through the flow path and out of the outlet of the liquid-free trap. The inlet can be open to ambient conditions.

Typically, the pressure of the gas stream at the rigid sintered hydrophilic material is about 1 atm.

In some versions of the methods, the gas stream is humidified prior to passing into the inlet of the liquid-free trap.

In some versions of the invention, the gas stream is the entire stream, for example, the entire stream of CDA or XCDA. In alternative versions of the invention, the gas stream is a portion (e.g., a representative sample) of the entire stream, for example, of CDA or XCDA.

In some versions of the methods described herein, the basic airborne molecular contaminant is an amine (e.g., a primary, secondary or tertiary water-soluble amine, ammonia, preferably ammonia).

In some versions of the methods described herein, the acidic airborne molecular contaminant is sulfur dioxide, a hydrogen halide (e.g., HF, HCl) or a water-soluble organic acid (e.g., acetic acid), or a combination of the foregoing.

EXEMPLIFICATION

Introduction

Process and equipment issues related to acidic and basic AMC in photolithography applications have been well documented, including reticle hazing (1), reaction with photoresist and corrosion (2). As the sensitivity of critical processes to AMC exposure in photolithography increases, the recommended allowable concentrations continue to decrease and AMC monitoring and concerns have expanded to areas outside of the lithography bay, to include electrochemical deposition, chemical mechanical planarization (CMP), wafer handling and dry etch. The International Technology Roadmap for Semiconductors (ITRS) recommends a minimum detection limit of 10 ppt for both acids and bases at the 22 nanometer (nm) node and these detection limits are expected to decrease to ppq levels with the introduction of 14 and 10 nm technologies (3). AMC controls and specifications for the introduction of extreme ultraviolet (EUV) lithography are currently still based on those of deep ultraviolet (DUV) lithography, but may change to push those limits further down, as new process or equipment sensitivities are discovered. All concentrations described herein are in volumetric (v/v), molar units (mol/mol), not mass based.

Real-time AMC monitoring solutions are desirable because they provide instantaneous and continuous measurement. However, even the most advanced technologies, such as ion mobility spectrometry (IMS), continuous wave cavity ring-down spectroscopy (CW-CRDS), photoacoustic spectrometry (PAS) and others can only achieve reliable detection limits in the ppb to high ppt range. In addition, sample transport, particularly of acidic compounds, is affected by line losses and reaction with bases. Finally, real-time monitors typically have substantial cost of ownership for maintenance, operation and calibration.

Traditionally, devices filled with deionized water, such as impingers (also known as bubblers) or open beakers have been the preferred sample trap method for the measurement of acidic and basic AMC. An impinger is a cylindrical container partially filled with liquid, (typically deionized water) that allows gas to be drawn through the liquid. As the gas passes through the liquid, soluble contaminants either react or dissolve into the liquid, dissociating into ionized species that can then be analyzed by ion chromatography. For example, hydrogen chloride gas (HCl) has a high dissociation constant and completely dissociates in water to form chloride anion (Equation 1):

$$HCl+H_2O \leftrightarrow H_3O^+ + Cl^- \qquad (1).$$

Although impingers are generally effective, the capture efficiency for different species varies and is dependent on and limited by several factors, including analyte solubility, dissociation constant of the dissolved species, evaporative losses, residence time of the gas within the mass transfer zone, bubble size and the potential for secondary reactions (formation of $HNO_X$, interference with dissolved $CO_2$, UV-catalyzed reactions, disproportionation of species and conversion from one species to another).

The mass transfer zone for gas diffusion within an impinger trap can be considered at the gas/liquid interface of each bubble as it travels through the liquid column. The longer the gas is in contact with that interface, the more gas can dissolve into the liquid. Bubble size and consistency has a significant impact on the capture efficiency of the trap since large bubbles may inhibit diffusion by preventing gas in the center of the bubble from reaching the mass transfer zone during its residence time in the water. A high density of very small bubbles, on the other hand, can also decrease transfer efficiency since many small bubbles can reduce the surface area of the mass transfer zone by effectively creating one large bubble. Combined, these factors limit the possible flow rate of the sample gas through the trap and trap size is limited by practical implementation considerations. This decreases detection capability by limiting the absolute amount of contaminant that can be collected during a given sample duration.

Impingers also undergo evaporative losses ranging from 0.1-0.5 ml/h depending on trap design, flow volume and moisture content of the sampled gas. This also limits sample time and decreases residence time of gas by reducing the height of the liquid column. Larger liquid volumes can be used to compensate for these evaporative losses, but this results in sample dilution and decreased detection capability, increasing sample times.

The standard analysis method for impinger trap solutions is ion chromatography (IC) with conductivity detectors. Quantitative measurement using ion chromatography is dependent on full dissociation of the ionized species. As indicated in Equation 1, hydrogen chloride is a strong acid, resulting in full dissociation and a 1:1 ratio of captured to detected chloride anions. However, when attempting to detect weak acids and bases, partial dissociation has been observed, resulting in non-linear response curves. This is another limitation of impingers as it may require secondary reactions (added chemicals) to produce the ionized species. For example, ammonia gas ($NH_3$) is a weak base in solution and only partially dissociates to form the ammonium ion (Equation 2):

$$NH_{3(g)} + H_2O \leftrightarrow NH_{3(aq)} NH_4^+ + OH^- \qquad (2).$$

The amount that does not dissociate and remains as aqueous ammonia in solution will not be detected by IC. The amount of gas that does not dissociate varies and depends on both temperature and total pH of the impinger solution, often resulting in measurement inconsistency.

Sulfur dioxide gas ($SO_2$) is technically an acidic gas acting as an electron acceptor (Lewis acid) and reacts with water through a complex mechanism producing a number of intermediate species in tautomeric equilibrium highly dependent on both pH and temperature (4). Oxidation of the resulting species by excess water or dissolved oxygen, autoprotolysis, and dimerization can further result in a number of secondary species, contributing to substantial variability and inconsistent measurement results. Finally, $SO_2$ was also found in an internal study to not quantitatively dissolve in pure water at air concentrations above 1 ppb without the aid of added peroxide to fully convert it to the dissolved form.

One persistent artifact associated with water impingers is the formation of "virtual $NO_X$", the ionic forms of nitrous and nitric acids from the dissolution of atmospheric $NO_X$ (the sum of NO and $NO_2$), which cannot be distinguished in single impingers from actual $HNO_2$ or $HNO_3$ and which frequently get reported as false positives. In prior studies, it was found that up to 1% of ambient $NO_X$ may get converted to $HNO_x$ (5). At ambient concentrations of several hundred ppb, that signal can be very substantial.

In addition to chemical limitations, impinger traps are also often subject to handling errors, inadvertent contamination and the potential for bacterial degradation, particularly if the liquid gets transferred between storage/transport and sampling vessels, a practice carried out by many labs. Water impingers have limited shelf life of a few weeks at the most, and are prone to bacterial contamination, particularly after being exposed to ambient air environments, and international shipping often causes customs delays based on the concern over the presence of liquid.

To address the disadvantages of impinger traps, a liquid-free adsorbent trap has been developed specific to both acidic and alkaline gas phase contamination. The specific liquid-free traps described in the Exemplification include porous substrates coated with either a bicarbonate ($NaHCO_3$) or phosphoric acid ($H_3PO_4$) solution, resulting in ionic capture of the AMC species and eliminating several problems associated with the dissolution based capture mechanism of liquid impingers.

Methodology

The liquid-free traps described herein capture acidic and basic compounds on a solid state medium that is coated with a base, for example, $NaHCO_3$, to capture acids or an acid, for example, $H_3PO_4$, to capture bases, and subsequent extraction of that medium in water, for example, deionized water, for analysis by IC. This adds one logistical step to the sample processing (dissolution of the captured ions in water) compared to water impingers, but has many advantages.

Each sample trap type was evaluated with common contaminants for the respective AMC class. Ammonia ($NH_3$) was selected as the alkaline test gas, since it is a weak base that remains a potential concern and is usually the highest concentrated or only base in most semiconductor environments. Hydrogen fluoride (HF), acetic acid ($CH_3COOH$) and sulfur dioxide ($SO_2$) were selected as acidic test gases. Hydrogen fluoride, as a moderately acidic inorganic species commonly found (often as an artifact from using PFA impinger materials and tubing), acetic acid, as the weakest common organic acid, and sulfur dioxide, for the reasons previously mentioned, were used to evaluate trap performance for all potential chemical behaviors.

Capacity

Trap capacity describes how much mass of an AMC species can be trapped before chemical reaction is exhausted and the compound can break through the trap without being retained. Capacity is a potential limitation of the sampling time at a given concentration or a limitation of the maximum concentration that can be sampled at a given sample time.

Because it is ultimately a function of both time and concentration, capacity is expressed in ppb-hours (ppb-h), which enables the calculation of either time or maximum concentration by using the amount that is known.

Initial testing was done by performing a titration of the extract as a proof of concept that some capacity for the target AMC did exist. Once feasibility was established, the trap was subjected to a known challenge at varying relative humidity and the capture efficiency (CE) was monitored over time and calculated as:

$$CE = \left(1 - \left(\frac{\text{Upstream}}{\text{Downstream}}\right)\right) * 100 \, (\%) \quad (3)$$

Trap capacity (in ppb-h) was then calculated by multiplying the total hours of testing (above a specified CE) by the challenge concentration. This is essentially the same process as determining the capacity or lifetime of a chemical filter.

The $NH_3$ challenge was created using a NIST traceable permeation device (122 ng/min $NH_3 \pm 4.99\%$ at 30° C., National Institute of Standards and Technology) and diluted to a concentration of approximately 10 ppb using purified clean dry air (Entegris® Gatekeeper® purifier CE700KF04RR). The stability of the upstream concentration was verified with a Total Molecular Base monitor (Extraction Systems Inc., TMB) prior to placing the sample trap in the gas stream. The TMB was then used to verify the downstream concentration at a measurement interval of 2 minutes until the CE had decreased below 90%. Sample flow through the traps during testing was approximately 0.7 liters per minute (lpm), pulled by the vacuum pump of the monitor.

The $SO_2$ upstream challenge was created using a NIST traceable permeation device (473 ng/min$\pm$2.77% at 40° C.) and diluted to a concentration of approximately 16 ppb using purified clean dry air (Gatekeeper purifier CE700KF04RR). The stability of the upstream concentration was verified with a Thermo Model 43i-TLE $SO_2$ monitor prior to placing the sample trap in the gas stream. The monitor was then used to verify the downstream concentration at a measurement interval of 5 minutes until the CE had decreased below 90%. Sample flow during testing was approximately 0.5 lpm, pulled by the vacuum pump of the monitor.

To create a variable humidity challenge, the purified clean dry air dilution gas was split and a controlled percentage was bubbled through ultra-pure water (UPW). The humidified portion of air was used for the humidity challenge. The downstream moisture level was verified by an in-line hygrometer (COLE-PARMER® 03313-66).

Accuracy and Precision

The precision and accuracy of liquid-free traps, standard liquid impingers (containing deionized water) and impingers spiked with 0.005M phosphoric acid were determined for comparison by taking multiple samples of a known $NH_3$ challenge. Acidification of impingers was done to maximize ionization of $NH_3$ for comparison to pure DI water devices.

The $NH_3$ challenge was created using the NIST traceable permeation device as above and output was diluted to a concentration of approximately 8 ppb using purified clean dry air adjusted to 40% RH. The stability of the upstream concentration was verified with the TMB prior to and during sampling.

The $SO_2$ capability of liquid-free traps, standard liquid impingers and impingers spiked with 3% $H_2O_2$ as an oxidative catalyst were determined for comparison by taking multiple samples of a known $SO_2$ challenge. The challenge was created using the NIST traceable permeation device as above and diluted to a concentration of approximately 16 ppb using purified clean dry air adjusted to 35% RH. The stability of the upstream concentration was verified with a Thermo Model 43i-TLE $SO_2$ monitor prior to and during sampling.

The HF testing of liquid-free traps and standard liquid impingers were compared by taking multiple samples of a known HF challenge, which was created using a NIST traceable permeation device (1971 ng/min$\pm$15% at 50° C.) and diluted to a concentration of 248 ppb$\pm$15% using purified clean dry air adjusted to 40% RH.

The $CH_3COOH$ testing was done with liquid-free traps and standard liquid impingers for comparison by taking multiple samples of a known $CH_3COOH$ challenge. The challenge was created using a NIST traceable permeation device (327 ng/min$\pm$2% at 35° C.) and diluted to a concentration of 13.3 ppb$\pm$2% using purified clean dry air adjusted to 25% RH.

The sample flow of all traps was controlled by pulling through a #14 orifice directly upstream of the trap with a vacuum pump (<15 Torr) resulting in a flow rate of 1.07 lpm.

The capture efficiency of the liquid-free trap also includes the extraction efficiency or recovery of the measured AMC from the solid media used to capture the AMC. A second series of testing was included as part of the initial testing to determine the extraction efficiency as a function of time and extraction conditions for $NH_3$.

In-Field Evaluation

The performance of sample traps in controlled laboratory conditions is an indication of optimal performance. However, when sampling in the field, the control of external conditions may not be ideal and the performance of the sample trap under less controlled conditions was evaluated. For method validation, the liquid-free traps were deployed to the field for both semiconductor environments and internal support, in parallel with standard impingers for comparison.

Sample Analysis

After sampling, the liquid-free trap solid media was transferred to a 30 ml HDPE container and extracted with deionized water and sonication. The extraction solution was then analyzed using a Thermo-Fisher® Dionex® ICS3000 ion chromatography system equipped with electrolytic suppression and conductivity detection. The anion channel of the system uses a potassium hydroxide eluent gradient with an AS19 250×2 mm analytical column and CRD200 carbonate removal device. The cation channel uses a methane sulfonic acid eluent gradient and CS19 250×2 mm analytical column.

The Hubaux-Vos method was used to statistically determine the instrument detection limit (IDL) and the method detection limit (MDL) with a 99% confidence interval. IDL was found to be 0.00026 mg/L $NH_4^+$ and MDL was found to be 0.00053 mg/L $NH_4^+$. The regression model had an $R^2$ value of 0.9998 and prob>F value of <0.0001, indicating the regression model was appropriate for the data. The residual plot did show some irregularity, but did not indicate any clear trend. The model is predicted to be quadratic regression based on the weak dissociation of ammonia in water (strong acids and bases with 100% dissociation are linear).

Results

Media Selection

A solid porous media was selected for its practicality, handling and preparation, as well as for coating with the capturing chemical and efficiency in capturing the AMC of concern in a single pass at the flow rates needed for detecting low concentrations of AMC. The actual solid porous material for the base trap is a low cost, one-use component of the trap that can be discarded after extraction.

Ultra-fine filtering type 316L stainless steel (SS) porous discs (available from Applied Porous Technologies, Inc. in 2, 5, 10, 20 and 40-micron pore sizes and dimensions of ½ inch diameter×1/16 inch width) were subjected to rinsing with deionized water and extraction for measurement of background contaminants. The results of the measurement are reported in the following table:

| Sample | Amount mg/L Lithium | Amount mg/L Sodium | Amount mg/L Ammonium | Amount mg/L Potassium | Amount mg/L Magnesium | Amount mg/L Calcium |
|---|---|---|---|---|---|---|
| Sintered Metal Disc in 5 ml Water (Pre-rinsed) | 0.0000 | 0.0008 | 0.0001 | 0.0059 | 0.0007 | 0.0462 |
| Sintered Metal Disc in 5 ml Water (Pre-rinsed) | 0.0000 | 0.0008 | 0.0001 | 0.0058 | 0.0007 | 0.0467 |

Some initial surface contamination was observed, but could be removed with a deionized water rinse. No amines were present in the rinsed sample.

GENPORE® surface-modified hydrophilic ultra-high molecular weight polyethylene (UHMWPE) solid phase extraction column frit (available under the part number 6mLPU and having an average pore size of 5-50 microns, a diameter of 0.513±0.005 inches and a depth of 0.125±0.020 inches was evaluated as a potential solid porous material. The use of a surface-modified hydrophilic PE increases polymer wettability by effectively reducing the contact angle to zero without changing the bulk properties of the material.

A number of chemicals for coating the solid porous media were investigated and it was concluded that bicarbonate and phosphoric acid were suitable for a number of reasons associated with ion chromatography handling, degradation of columns, interference with detected compounds and speed of analysis, as well as coating of the media.

Citric acid was also evaluated as a coating material. A 5% citric acid solution was used to chemically treat the sintered 316L SS media discussed above. Citric acid was selected based on the following properties: it is a polyprotic, water-soluble acid (which may increase the number of potential active sites); it is less than a C6 organic acid (high molecular weight organics, greater than C6, can potentially contaminate the IC suppressor, forming a film on the membrane); it is a weak acid (eliminating potential interference caused by strong acids, such as sulfuric acid and hydrochloric acid, with the ion-exchange resin of the IC column); and the anion is stabilized by intra-molecular hydrogen bonding from other protic groups in citric acid.

To test the capacity of the treated material, treated media was extracted with 30 mL water. The citric acid deposited in the pore structure of the media should dissolve into water, decreasing the pH of the solution. The amount of citric acid was then calculated from the volume of 0.005 M NaOH titrant used to reach the equivalence point. 5% phenolphthalein in 50% ethanol was used as an indicator. A theoretical capacity of 1.87 mg ammonia was calculated from the amount of 0.005 M NaOH titrant used to reach the equivalence point for the solution resulting from the extraction of the sintered 316L SS media.

Although the SS media had a low background contamination levels and a high theoretical capacity, the low ionization energies of Group 1 and 2 metal impurities in the media resulted in an increase in dissolved metal cations. Although not wishing to be bound by any particular theory, the presence of the citric acid is thought to facilitate the mobility of the metallic ions out of the media and into the deionized water used for extraction, resulting in IC interference and preventing the quantitation of $NH_4^+$.

| Acid Trap Preparation | | | |
|---|---|---|---|
| Material | Supplier | Part Number | Specification |
| Assembly Substrate | Entegris Applied Porous | ESI005971 10233-200 | Machined PEEK Porous Metal Disc Dimensions: 0.500" × 0.125" Material: 316LSS Porosity: 20 micron |
| Chemical Coating | N/A | N/A | 0.1M Sodium Carbonate ($Na_2CO_3$) Anhydrous CAS 497-19-8 (>99.99% trace metals purity and <10 mg/kg trace anion $Na_2CO_3$ powder) |

Prior to chemical treatment, the 316LSS substrate material was rinsed a minimum of three times with deionized water (18.2 mΩ) to remove soluble surface contamination. After the rinse, the material was ultrasonically cleaned in deionized water for a minimum of 1 hour to allow penetration into the pore structure of the material. The material was rinsed a minimum of three more times with deionized water before being allowed to dry completely in a chemically clean, purified XCDA purged oven at 65+/−5° C.

500 mL of a 0.1M $Na_2CO_3$ solution was prepared by adding 5.03 g of anhydrous sodium carbonate (CAS 497-19-8) to 500 mL deionized water.

The 316LSS substrate was thoroughly rinsed in 250 mL of the 0.1M sodium carbonate solution by vigorously shaking in a closed, chemically clean container for a minimum of 60 seconds. The rinse solution was decanted and the rinsed substrate was ultrasonically treated in the remaining 250 mL of $Na_2CO_3$ solution for a minimum of 15 minutes. The substrate and solution was poured through a HDPE mesh screen that had been thoroughly rinsed to remove surface contamination, and the solution was allowed to pass through the mesh to waste while the coated media was collected on the screen. The HDPE mesh screen was placed into a purified XCDA purged oven at 30° C. (the media should be evenly distributed to allow uniform drying) until the media is completely dry. Although not wishing to be bound by any particular theory, it is believed that treatment of the solid porous media results in the formation of the hydrated salt of sodium carbonate. Sodium carbonate decahydrate is stable at room temperature but re-crystallizes at 32° C. to sodium carbonate heptahydrate, $Na_2CO_3 \cdot 7H_2O$, then above 37-38° C. to sodium carbonate monohydrate, $Na_2CO_3 \cdot H_2O$.

Treated media was stored in a sealed, chemically clean container below 30° C. to prevent dehydration of the crystallized $Na_2CO_3 \cdot xH_2O$ treatment[1] and intrusion of ambient contamination. Treated media can be stored for 60 days.

A second acid trap, which was used in the experiments described herein, was made in accordance with the procedure outlined above for the sodium carbonate acid trap using sodium bicarbonate instead of sodium carbonate.

| Base Trap Preparation | | | |
|---|---|---|---|
| Material | Supplier | Part Number | Specification |
| Assembly Substrate | Entegris GenPore® | ESI005971 6mLPU Hydrophilic | Machined PEEK Porous Hydrophilic Polymer Dimensions: 0.513" × 0.125" Material: Hydrophilic UHMW-PE Porosity: 5-50 micron |
| Chemical Coating | N/A | N/A | 0.05M Ortho-phosphoric Acid ($H_3PO_4$) Crystalline CAS 7664-38-4 (>99.999% trace metals purity) |

The GenPore® hydrophilic media does not require pretreatment. Rinsing the media prior to use will remove the hydrophilic coating, making the media unsuitable for the intended application.

500 mL of a 0.05M $H_3PO_4$ solution was prepared by adding 2.45 g of crystalline ortho-phosphoric acid (CAS 7664-38-4) to 500 mL deionized water.

The GenPore® substrate was thoroughly rinsed in 250 mL of the 0.05M ortho-phosphoric acid solution by vigorously shaking in closed, chemically clean container for a minimum of 60 seconds. The rinse solution was decanted and the rinsed substrate was treated ultrasonically treated in the remaining 250 mL of $H_3PO_4$ solution for a minimum of 15 minutes. The substrate and solution were poured through a HDPE mesh screen thoroughly rinsed to remove surface contamination, allowing the solution to pass through the mesh to waste and the coated media to be collected on the screen. The HDPE mesh screen was placed into a purified XCDA purged oven at 30° C. (the media should be evenly distributed to allow uniform drying) until the media is completely dry. Although not wishing to be bound by any particular theory, it is believed that treatment results in the formation of the crystalline phosphoric acid within the pore structure of the media. Ortho-phosphoric acid hydrate is stable at room temperature but has a melting point of 30° C., while the anhydrous crystalline solid melts at 42° C.

Treated media was stored in a sealed, chemically clean container below 30° C. to prevent the crystallized $H_3PO_4$ from melting and intrusion of ambient contamination. Treated media can be stored for 60 days.

Trap Assembly

Figure 1B:
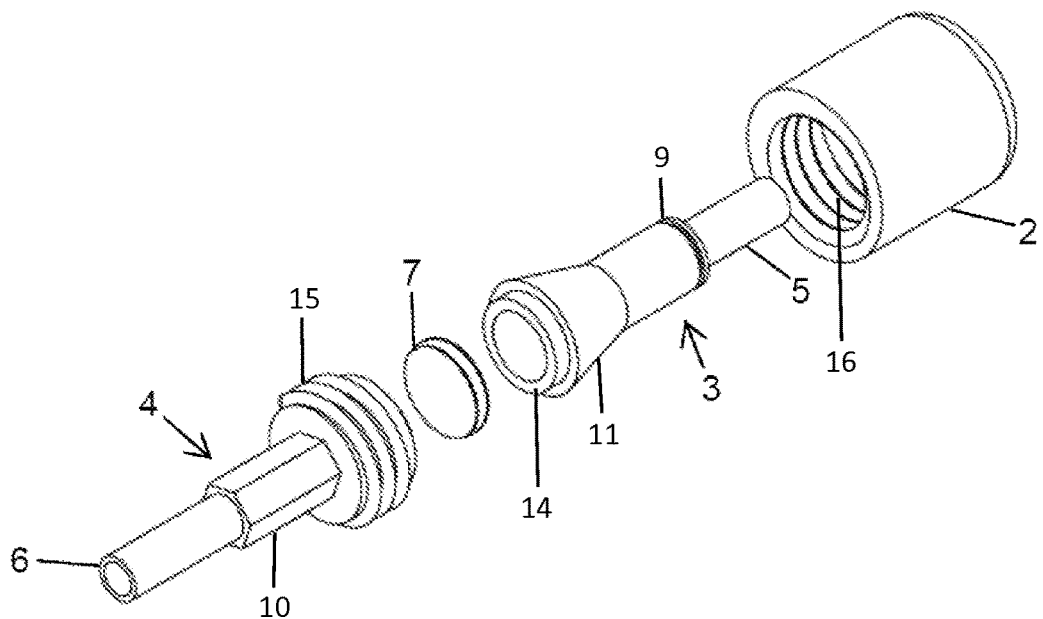
FIG. 1B is an exploded view of a liquid-free trap assembly in one version of the invention.
Figure 1C:
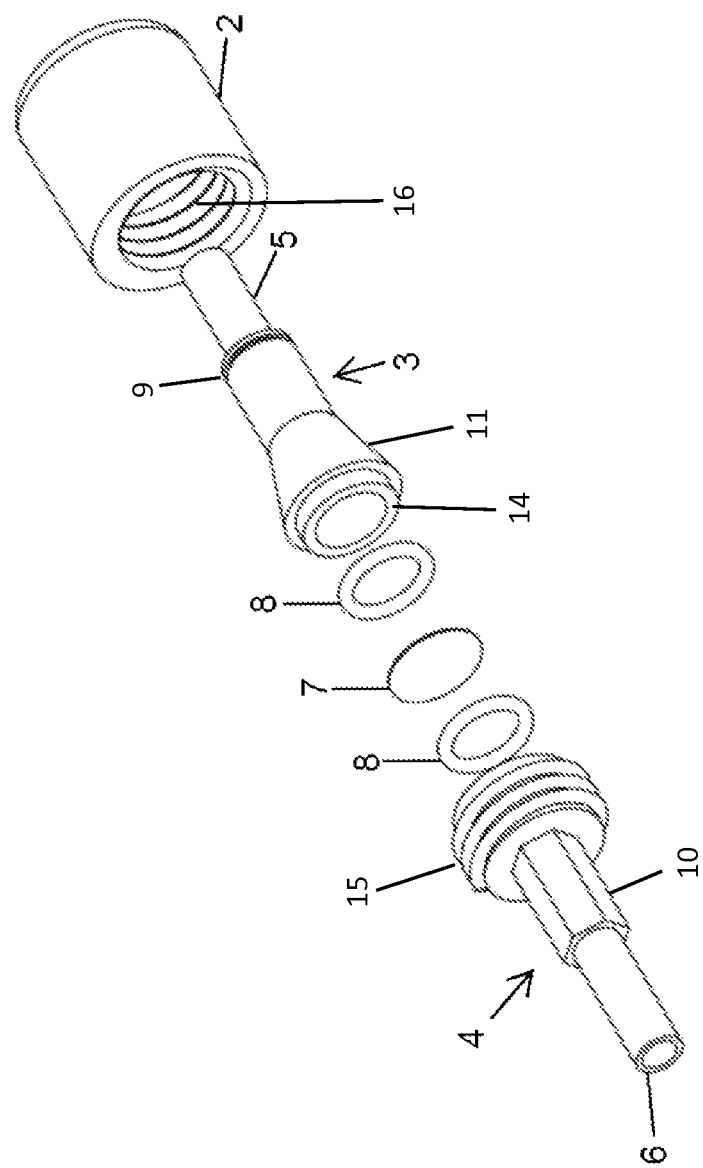
FIG. 1C is an exploded view of a liquid-free trap assembly in one version of the invention.
Figure 1D:
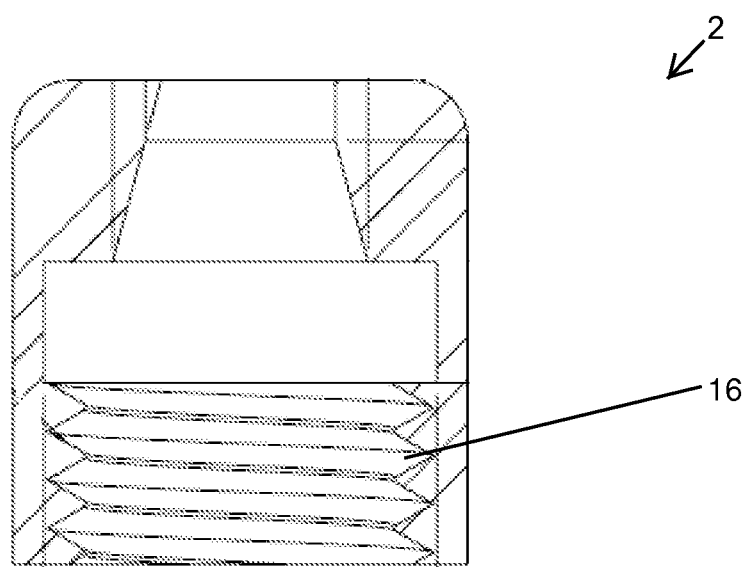
FIG. 1D is another view of the locking nut in FIGS. 1A-1C.
Figure 1E:
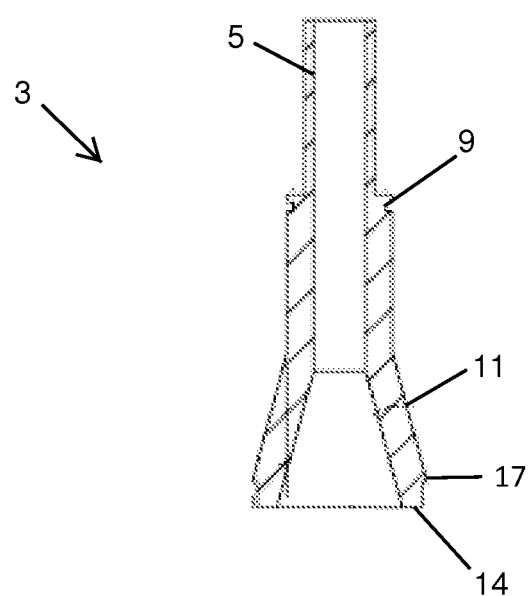
FIG. 1E is another view of the upstream component of at least FIGS. 1A and 1B.
Figure 1F:
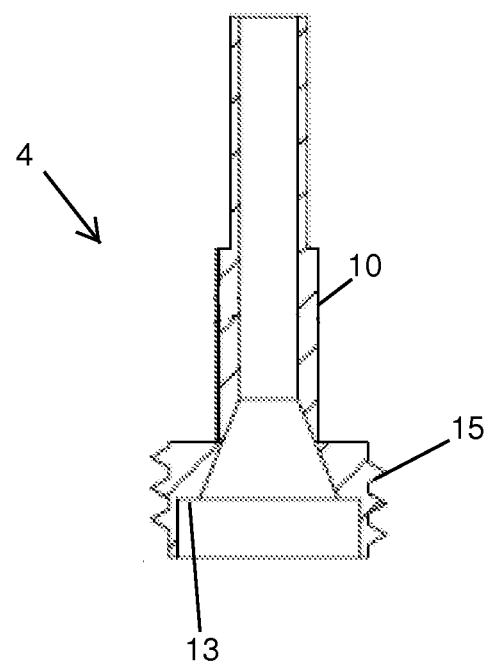
FIG. 1F is another view of the downstream component of at least FIGS. 1A and 1B.
Figure 1G:
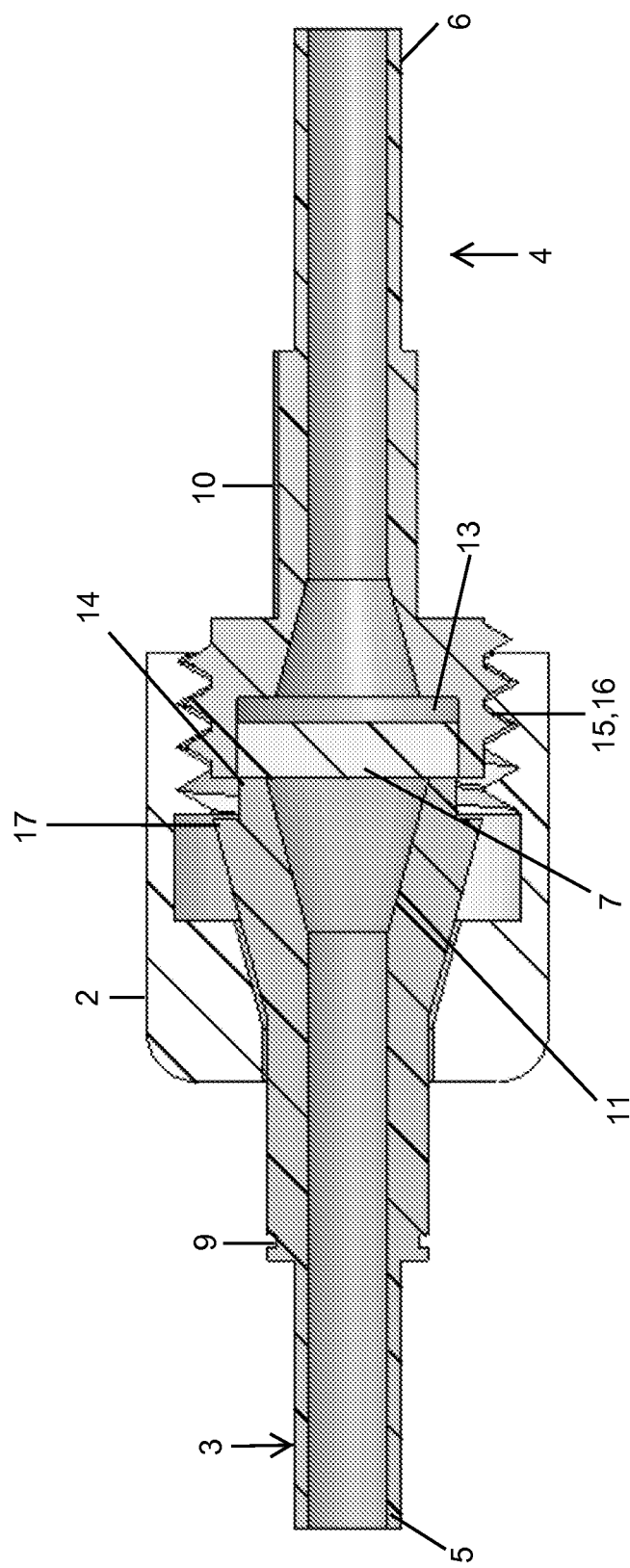
FIG. 1G is a transparent, assembled view of a liquid-free trap in one version of the invention.

The trap was assembled as shown in FIG. 1B. TEFLON®-coated forceps were used to handle the media, minimizing surface contact by securing the disc on its side. A 5/16" wrench was used to tighten the locking nut a quarter turn past initial tightness to ensure a proper seal with the media.

Media Extraction

The trap was opened by unscrewing the locking nut. The trap was held vertically with bottom assembly on the bottom. The top assembly was separated from the bottom assembly so that the media remained within the bottom assembly. The bottom section was inverted and the media allowed to fall into a 30 mL sample vial by aligning the inverted bottom assembly over the mouth of the sample vial. If the media became stuck in the assembly, a chemically clean push rod was inserted into the trap opening and used to push the media into the vial.

6 mL of 18.2 mΩ deionized water was pipetted into the sample vial containing the media. The extraction was begun by vigorously shaking the closed sample vial for a minimum of 60 seconds before ultrasonically treating the media in the extraction solution for a minimum of 4 hours. Sample vials were then stored or analyzed in accordance with the appropriate analytical method.

The sample trap housing used in these experiments is made from polyether ether ketone (PEEK). A sample liquid-free trap housing is depicted in FIG. 1A and an assembly drawing of a liquid-free sample trap is depicted in FIG. 1B. Liquid-free trap housing 1 in FIG. 1A and in the housing used in these experiments is a three piece design that provides sealing and secure retention of the solid porous material, optimized internal flow channeling and easy preparation and handling. Housing 1 includes locking nut 2, upstream component 3 and downstream component 4. Upstream component 3 and downstream component 4 each have tube ends, 5 and 6, respectively. The tube ends in the trap used in these experiments have a 6.4 mm OD and can be capped with standard tube fittings for transport and storage. Length of the trap can be chosen to match that of commercially available organic traps made from stainless steel or glass. Internal design is optimized for flow, handling and minimized contamination.

Ammonia Capacity

With diffusion and dissolution of the sample gas to a liquid eliminated, ammonia capture is based on a simple acid/base reaction and capacity in liquid-free traps is primarily determined by the number of active sites for ionic bonding, i.e., the amount and nature of acid used to coat the porous material, where the $NH_3$ forms a combination of the mono-ammonium and diammonium salts on the surface of the substrate (Equation 4). The tri-ammonium salt is unstable.

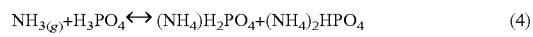

$$NH_{3(g)} + H_3PO_4 \leftrightarrow (NH_4)H_2PO_4 + (NH_4)_2HPO_4 \qquad (4)$$

Trap capacity for $NH_3$ was determined to be 200 ppb-h at 0% relative humidity. For typical 0% RH applications, such as supply and process gas lines, trap capacity is more than one hundred times what is required for typical tool OEM specifications and ITRS recommendations for allowable AMC concentrations. Entegris Analytical Services typically finds less than 1 ppb of AMC in CDA and $N_2$ lines, but process gases may contain higher levels.

The addition of moisture at 40% relative humidity increased trap capacity to 350 ppb-h. The increase in capacity by adding moisture results from the ability of water to lower the free energy of formation for the reaction and as a secondary consequence may provide a means for ion mobility within the media. Capacity for $NH_3$ was determined at the 99% capture efficiency level, i.e., less than 1% breakthrough.

Figure 2:
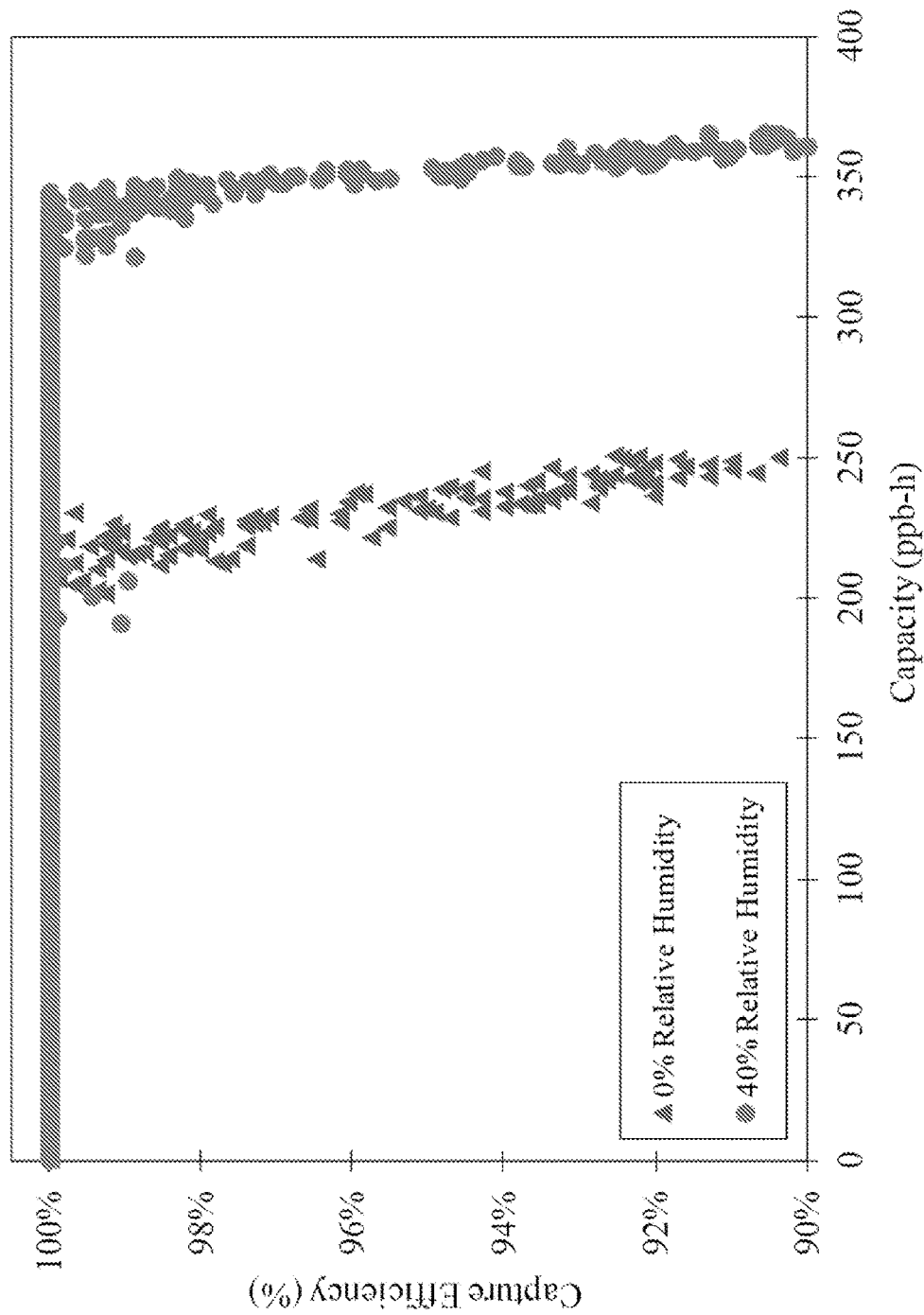
FIG. 2 is a graph of capture efficiency as a function of trap capacity, and shows the ammonia capacity of a liquid-free base trap at 0% and 40% RH.

FIG. 2 is a graph of capture efficiency as a function of trap capacity, and shows the ammonia capacity of the liquid-free base trap at 0% and 40% RH.

Given modern supply gas concentrations of less than 1 ppb and typical clean room concentrations of less than 10 ppb of $NH_3$, the measured capacity translates to a quantitative capture of $NH_3$ for 20-35 hours of sampling at 3.5 lpm, much in excess of what is required for ppq-level analysis. This allows for the sampling of AMC within one work shift and without the need for 12-72 hour sampling time typically used.

Alkaline capacity is a function of the number of acidic active sites for ionic bonding (in this case the $1^{st}$ and $2^{nd}$ protons of $H_3PO_4$) and can be extended to other compounds with similar chemical behavior, like amines (Equation 5).

$$\text{Capacity(Mol Eq.)} = \left(\frac{\text{Number of Active Sites}}{|\text{Net Ionic Charge}|}\right) \quad (5)$$

Equation 5 is believed to provide a rough estimate for amine capacity. However, $pK_b$ of the alkaline species and steric hindrance due to larger molecule size can be considered. As an approximation, it is estimated that the same capacity for amines or any combination of ammonia and amines can be collected.

Sulfur Dioxide Capacity

Figure 3:
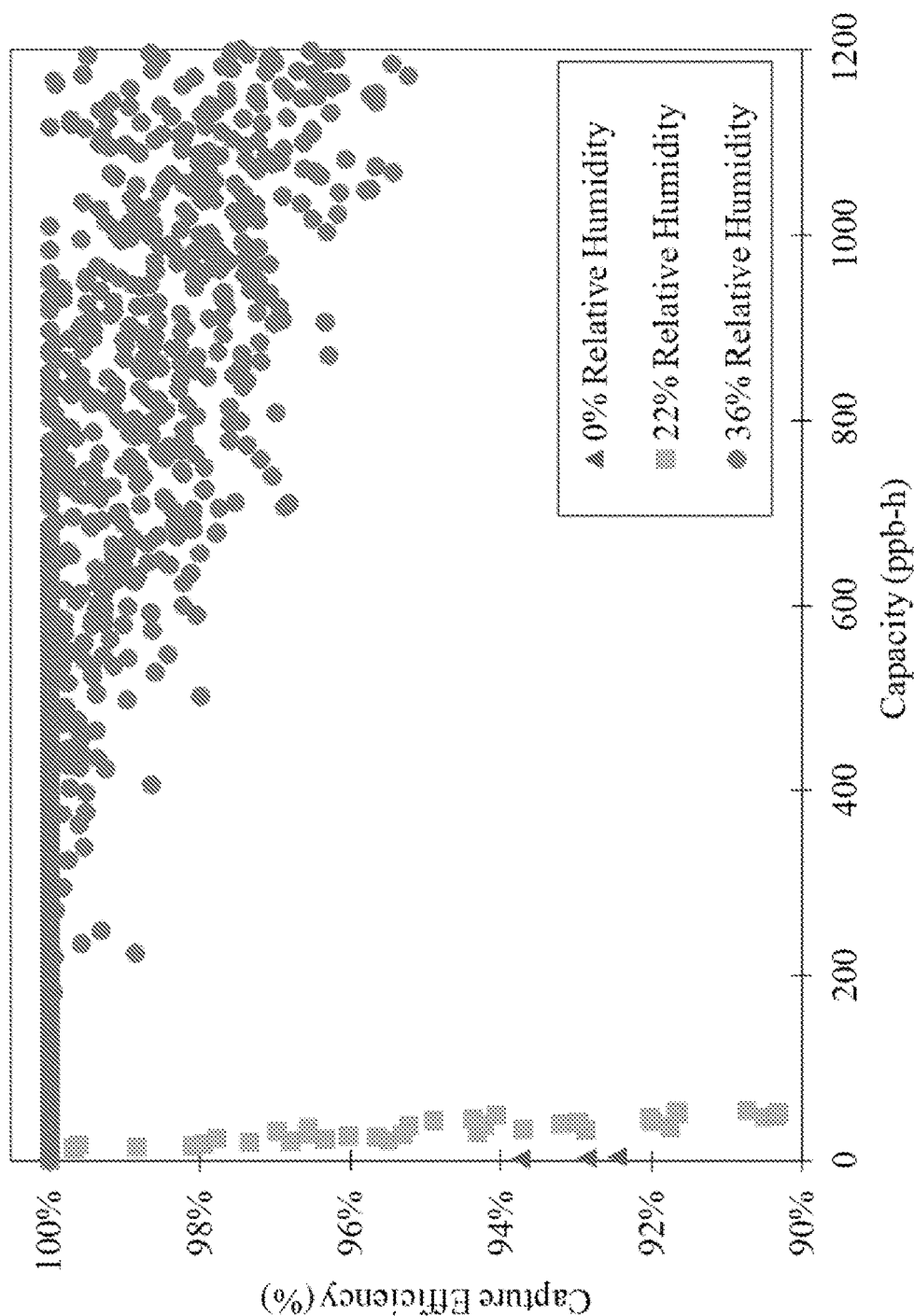
FIG. 3 is a graph of capture efficiency as a function of capacity, and shows the $SO_2$ capacity of a liquid-free acid trap at 0%, 22% and 35% RH.

Trap capacity for $SO_2$ was determined to be 5 ppb-h at 0% RH and 90% capture efficiency. The addition of moisture at 22% relative humidity increased trap capacity to 60 ppb-h for 90% CE, and at 35% relative humidity trap capacity increased to more than 400 ppb-h for 99%. FIG. 3 is a graph of capture efficiency as a function of capacity, and shows the $SO_2$ capacity of a liquid-free acid trap at 0%, 22% and 35% RH.

For typical dry applications, like process gas lines, trap capacity is sufficient to meet requirements for typical tool OEM specifications and ITRS recommendations (typically in the ppt range). Entegris Analytical Services does not find $SO_2$ to be elevated above 1 ppb even in fairly outdated semiconductor environments. Hence, the capacity is considered sufficient and not a limitation for sample time.

Without wishing to be bound by any particular theory, the proposed mechanisms to describe the capture of $SO_2$ on the dry media involves an initial reaction of $SO_2$ with excess water to produce the intermediate bisulfite ion (Equation 6), the primary reaction product in a pH range of 2 to 8.

$$SO_{2(g)} + H_2O \leftrightarrow HSO_3^- + H^+ \quad (6)$$

The resulting bisulfate ion is then free to react with $NaHCO_3$ on the surface of the media to form the sodium sulfate salt (Equation 7).

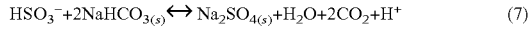

$$HSO_3^- + 2NaHCO_{3(s)} \leftrightarrow Na_2SO_{4(s)} + H_2O + 2CO_2 + H^+ \quad (7)$$

Even at 0% RH, there is some capacity for $SO_2$ due to direct ionic bonding and the presence of crystalline water bound to $NaHCO_3$ as the decahydrate salt ($NaHCO_3 \cdot 10H_2O$). The resulting sodium sulfate salt completely dissociates in the extraction solution and was quantified as $SO_4^{2-}$ using established ion chromatography methods. It is expected that acidic species, that directly interact with $NaHCO_3$ to form immediate ionic bonds and do not depend heavily on the presence of moisture, will have significantly improved capacity at lower relative humidity.

Ammonia Accuracy and Precision

The standard water impinger had an average capture efficiency of 88% for $NH_3$ at 40% RH in relation to the calculated and monitor-verified challenge concentration of 8.0 ppb. Although not wishing to be bound by any particular theory, the decreased capture efficiency in a standard impinger likely results from the partial dissociation of ammonia in solution (Equation 2) and/or incomplete diffusion from the air bubbles into the water column. A decrease of pH of the solution results from either a decreasing ammonia concentration or the presence of an acidic species and has a direct effect on the ionization of ammonia, shifting the equilibrium increasingly towards ammonium formation. This results in the characteristic non-linear calibration curve for ammonia and amines in ion chromatography analysis.

This theory is corroborated by the test results from the pH adjusted impinger, which was spiked with 0.005M phosphoric acid and which had an average capture efficiency of 95.1% for $NH_3$ at 40% RH, the remaining 5% likely attributed to inadequate capture efficiency. The increased concentration of phosphate counterions in the pH adjusted solution facilitates better conversion of the dissolved ammonia to the fully dissociated ammonium ion. Based on this, it can be predicted that the $NH_3$ capture efficiency of the impinger will continue to decrease with increasing ammonia when sampling with water impingers. This phenomenon is particularly disadvantageous for use in semiconductor fabs with older technology nodes, where concentrations above 10 ppb are found, or non-lithobay process areas with increased ammonia levels.

The liquid-free trap had an average capture efficiency of 99.8% for $NH_3$ at 40% RH with the lowest trap to trap variability (standard deviation of 7.6%) of the three traps tested. The chemical mechanism of the liquid-free trap media is based on the formation of ionic bonds (Equation 4) and is not subject to the limitations of dissolution-based capture. Instead, the only limitations result from its capacity, which was shown to be sufficient.

Figure 4:
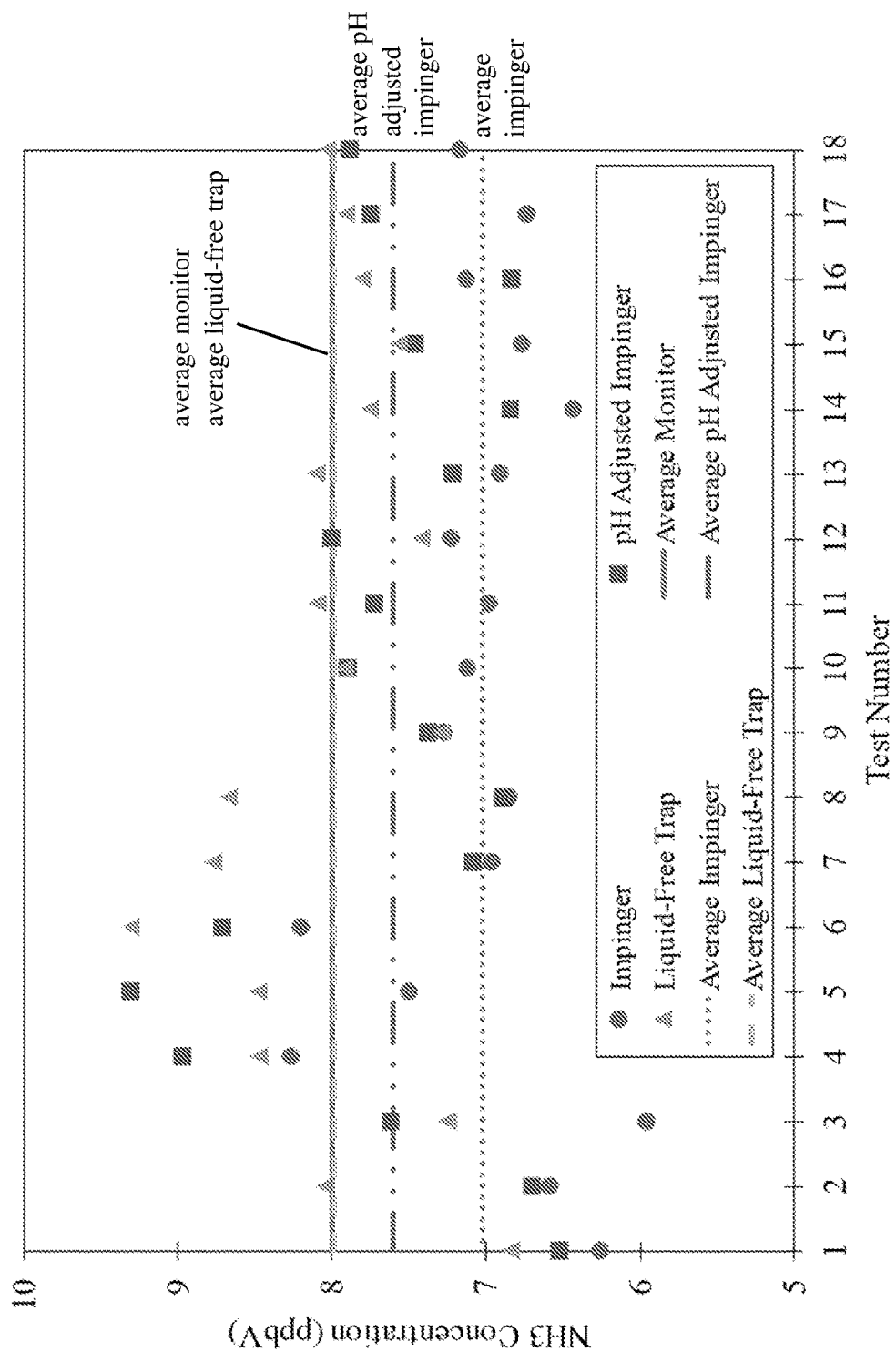
FIG. 4 is a graph of ammonia capture efficiency as a function of test number, and shows the ammonia capture efficiencies of a standard impinger, a pH-adjusted impinger and a liquid-free trap according to the invention.

The results of the ammonia accuracy and precision comparison are reported in Table 1 and depicted graphically in FIG. 4.

TABLE 1

| Sample Trap | Average Measured $NH_3$ Concentration (ppb) | Relative Standard Deviation | Capture Efficiency |
|---|---|---|---|
| Standard Impinger | 7.02 | 8.3% | 87.8% |
| pH Adjusted Impinger | 7.61 | 10.3% | 95.1% |
| Liquid-Free Trap | 7.99 | 7.6% | 99.8% |
| TMB Monitor | 8.00 | 2.3% | 100% |

Sulfur Dioxide Performance

Standard water impingers had an average capture efficiency of 91% for $SO_2$ at 36% RH for a challenge concentration of 16.8 ppb. However, this average is skewed heavily by the presence of one outlying data point (manifested in a high standard deviation), which, if excluded, would reduce the capture efficiency to 86%. The low capture efficiency results from the formation of multiple intermediate species in solution and the decreased ionization with increasing concentration of those intermediate species. This would indicate that the capture efficiency is inversely proportional to concentration and will decrease as the total $SO_2$ concentration increases. The formation of sulfite and sulfate anions will also act to acidify the impinge, shifting the equilibrium increasingly towards the gas phase as the pH of the solution decreases. The data from the sulfur dioxide performance tests are summarized in Table 2.

TABLE 2

| Sample Trap | Average Measured $SO_2$ Concentration (ppb) | Relative Standard Deviation | Capture Efficiency |
|---|---|---|---|
| Standard Impinger | 15.3 | 16.7% | 91.1% |
| Impinger with 1% $H_2O_2$ | 16.7 | 5.1% | 99.4% |
| Liquid-Free Trap | 16.3 | 4.9% | 96.5% |
| $SO_2$ Monitor | 16.8 | 3.7% | 100% |

Water impingers spiked with 1% $H_2O_2$ performed substantially better than standard water impingers, with an average and more consistent capture efficiency of 99.4%. The improved performance may be a result of the peroxide fully oxidizing both undissociated $SO_2$ and partially oxidized species in solution and facilitating complete conversion to the sulfate ion (Equation 9).

$$SO_2 + H_2O_2 \leftrightarrow 2H^+ + SO_4^{2-} \quad (9)$$

The liquid-free trap had an average capture efficiency of 96.5% for $SO_2$ at 36% RH, with the smallest amount of trap to trap variability of 4.9% relative standard deviation. Although the 1% $H_2O_2$ impinger had higher capture efficiency, the added peroxide is an additional process step and can be detrimental to the ion-exchange resin used in the analytical columns of the IC system, posing a disadvantage for routine analysis. In addition, the presence of peroxide can also oxidize atmospheric gases, including NO and $CO_2$, creating artifacts and altering impinger chemistry.

$$2NO + 3H_2O_2 \rightarrow 2H^+ + 2NO_3^- + 2H_2O \quad (10)$$

$$CO_2 + 2H_2O_2 \rightarrow H^+ + HCO_4^- + 2H_2O \quad (11)$$

The reactions identified in Equations 10 and 11 are minimized by the liquid-free trap due to the absence of a source for further oxidation.

Performance for HF

For the capture of HF, the water impinger had a capture efficiency of 98.2% and the liquid trap 100.2% for air sampled at 40% RH. The liquid-free trap had a slightly better precision than the impinger with a 3.5% standard deviation. The high capture efficiency of the impinger is expected since HF is fully miscible with water in all proportions and interacts through hydrogen bonding, unlike other hydrogen halides. The primary mechanism of capture on the liquid-free trap is purely an ionic reaction (Equation 12).

$$NaHCO_{3(s)} + HF_{(g)} \rightarrow NaF_{(s)} + CO_{2(g)} + H_2O_{(l)} \quad (12)$$

The results of HF performance experiments are summarized in Table 3.

TABLE 3

| Sample Trap | Average Measured HF Concentration (ppb) | Relative Standard Deviation | Capture Efficiency |
|---|---|---|---|
| Standard Impinger | 244 | 5.5% | 98.2% |
| Entegris Liquid-Free Trap | 249 | 3.5% | 100.2% |
| Permeation Device (Calculated) | 248 | 15.0% | N/A |

These results differ from previously reported results for impingers and liquid-free trap technology, which indicated significantly lower capture efficiencies for both types of trap (6). This may be a result of the moisture content of the sample gas and is supported by the behavior of HF at low concentrations in the presence of water. It has been shown that the primary solute species is the H—H bonded ion pair $[H_3O^+.F^-]$, which facilitates dissociation and increases HF solubility (7).

Acetic Acid Performance

For the capture of acetic acid, the standard impingers had an average capture efficiency of 98.2% at 36% RH and a 4.1% relative standard deviation. The liquid-free trap had about the same capture efficiency of 96.1% and slightly higher variability when compared to the standard impinger. There is no reason to expect a decreased performance specifically for $CH_3COOH$ since it is captured primarily through ionic bonding (Equation 13) but the fairly high $pK_a$ (weak acidity) of acetic acid may contribute to the capture efficiency being less than 100%.

$$NaHCO_3 + CH_3COOH \leftrightarrow NaCH_3COO^- + CO_2 + H_2O \quad (13)$$

Nevertheless, this is considered to be a sufficient result for acetic acid monitoring in the semiconductor industry. The results of the acetic acid performance tests are summarized in Table 4.

TABLE 4

| Sample Trap | Average Measured Acetic Acid Concentration (ppb) | Relative Standard Deviation | Capture Efficiency |
|---|---|---|---|
| Standard Impinger | 13.1 | 4.1% | 98.2% |
| Liquid-Free Trap | 12.8 | 5.7% | 96.1% |
| Permeation Device (Calculated) | 13.3 | 2.0% | N/A |

In-Field Evaluation

The performance of sample traps in controlled laboratory conditions is an indication of optimal performance. However, when sampling in the field, the external conditions may not be ideal and sampling can involve sample operator handling, shipping, etc.

Figure 5A:
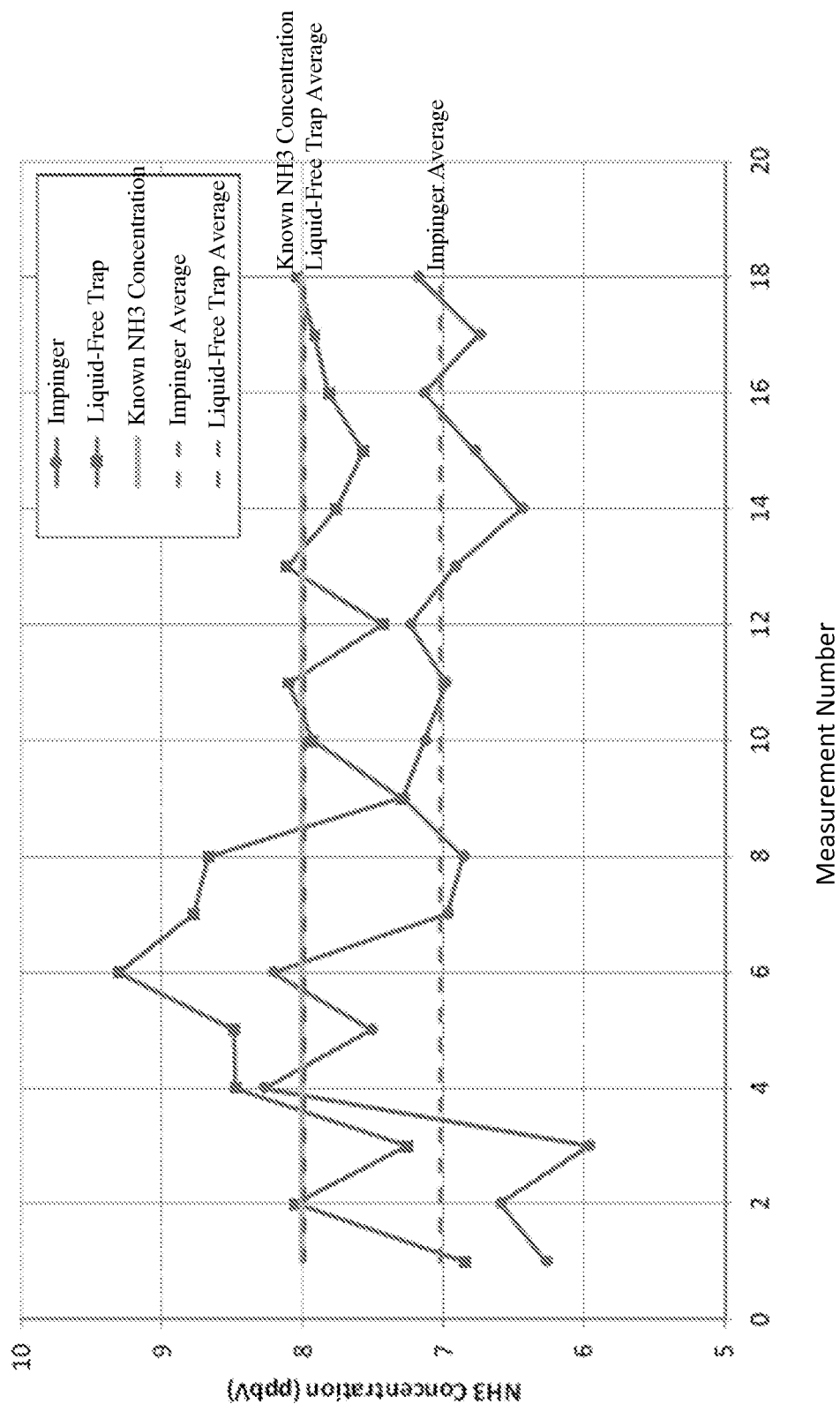
FIG. 5A is a graph of ammonia concentration as a function of measurement number for a known ammonia gas source, and shows that the concentration of ammonia measured by an impinger was consistently lower than the known ammonia concentration and lower than the ammonia concentration measured by a liquid-free trap.

The performance of the liquid-free trap under less controlled conditions was evaluated for $NH_3$. The liquid-free traps were both deployed to the field for both external customers and internal support and sampled in parallel with standard impinger traps. Both trap types showed a repeatability of about 5% between measurements. However, impingers showed capture efficiencies consistently 5-20% lower than those of the liquid-free traps, resulting in an average 10.2% difference between the two traps in more than 100 real-world data points over a concentration range spanning five orders of magnitude, between <10 ppt and 0.1 ppm. FIG. 5A is a graph of ammonia concentration as a function of measurement number for a known ammonia gas source, and shows that the concentration of ammonia measured by impingers was consistently lower than the known ammonia concentration and lower than the ammonia concentration measured by the liquid-free trap.

The correlation of the two trap types is 0.98, indicating that the data sets for the two traps are statistically not significantly different. An ANOVA analysis of the data produced a $M_{Measured}=0.0094$, $F_{Crit}=3.9$ and P-value=0.92, indicating a confirmation of the null hypothesis, that data are not statistically different. Nevertheless, the 7.6% difference indicated by the slope of the line likely reflects the approximately 10% increase in measured capture efficiency of the liquid-free trap compared to the standard impinger (see Table 1).

Figure 5B:
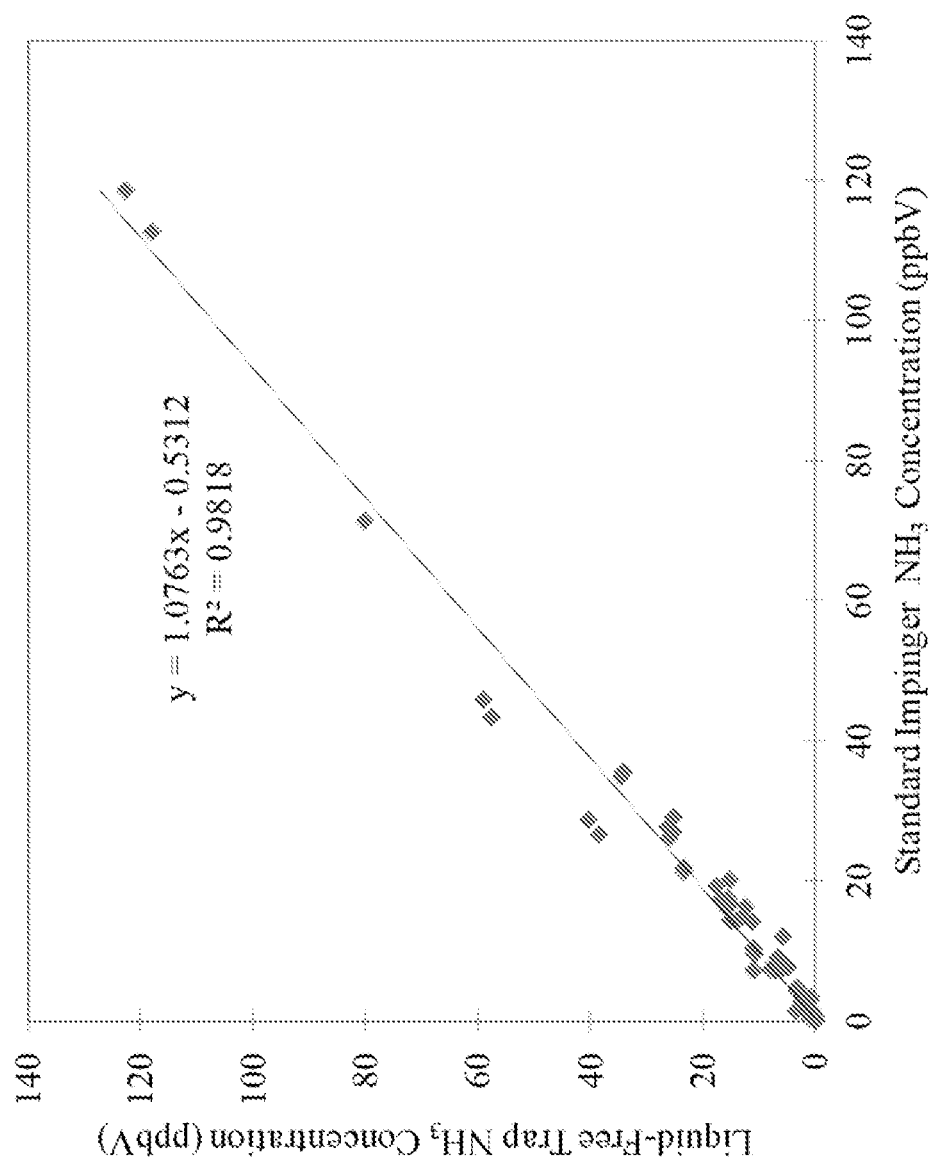
FIG. 5B is a correlation plot of the captured ammonia concentration for a liquid-free trap and a standard impinger, and shows that the data sets for the two traps are not statistically significantly different.

FIG. 5B is a correlation plot of the captured ammonia concentration for the liquid-free trap and a standard impinger, and shows that the data sets for the two traps are not statistically significantly different.

Shelf Life

Shelf life of the liquid-free trap has been studied by preparing a number of coated substrates and then storing these over a period of three months, analyzing redundant samples every week to observe potential trends. The data suggest that liquid-free traps can be stored in chemically clean containers and refrigerated for up to three months without impact above the detection level. A plot of the data indicated no increasing trend in the $NH_3$ concentration during storage. This shelf life matches that of organic AMC traps and enables quicker dispatch and onsite storage for immediate deployment.

CONCLUSIONS

To address the disadvantages of water-filled impinger traps, a liquid-free adsorbent traps specific to both acidic and alkaline gas phase contamination has been developed. Capacity results for the liquid-free base trap for ammonia yielded more than 200 ppb-h at 100% capture efficiency without any moisture (simulating sampling of CDA or $N_2$) and 350 ppb-h at 40% RH. Capacity results for sulfur dioxide were highly dependent on the moisture content of the sampled gas: at 0% relative humidity, capacity yielded only 5 ppb-h at 90% capture efficiency, but increased exponentially to more than 1200 ppb-h at 40% relative humidity. HF and acetic acid performance was satisfactory and matches that of standard impingers.

Given modern supply gas concentrations of less than 1 ppb and cleanroom concentrations of less than 10 ppb, both acid and base capacity significantly exceeds what is found in related environments and what is required for low-level analysis. Trap performance allows for the sampling and analysis of ppq-level AMC within one work shift and without the need for 12-72 hour sampling typically applied by most labs in the industry.

Performance testing indicates that the liquid-free trap provides both more precise and more accurate results for $NH_3$, $SO_2$ and HF in comparison to the standard impinger in lab testing, with a relative standard deviation not exceeding 8% and capture efficiency greater than 95% for all three compounds. Acetic acid was the only compound that shows slightly decreased performance but still maintained a precision and accuracy fully suitable for the application.

Deployment to the field at both external customer sites and internal support applications in parallel with standard impinger traps resulted in up to 10% difference between the trap types, providing the necessary evidence that liquid-free traps are suitable for impinger replacement.

The liquid-free traps disclosed herein represent a substantial improvement over existing sampling techniques based on easier in-field handling, reduced contamination through handling, extended shelf life and eliminated concerns over shipping liquids.

REFERENCES (1) Grenon B., Bhattacharyya K., Volk W., Phan K., Poock A., "Reticle surface contaminants and their relationship to sub-pellicle defect formation", *Proceedings of SPIE, Metrology, Inspection and Process control for Microlithography XVIII*, Vol. 5375, pp. 355-62, (2004).

(2) Dean, K. R., Miller, D. A., Carpio, R. A., Petersen, J. S., & Rich, G. K., "Effects of Airborne Molecular Contamination on DUV Photoresists", *Journal of Photopolymer Science and Technology*, 10(3), pp. 425-443, (1997).

(3) International Roadmap Committee (IRC), *ITRS Yield Enhancement Table*, Table YE4 "AMC Monitoring Methods" (2012).

(4) Gutherie, P. "Tautomeric equilibria and $pK_a$ values for 'sulfurous acid' in aqueous solution: a thermodynamic analysis", *Canadian Journal of Chemistry*, 57, pp. 454 (1979).

(5) Lobert, Jürgen M., Grayfer A. and Oleg K., "Virtual $NOx^-$: A Measurement Artifact in Wet Impinger Air Sampling.", Entegris Application Note APN000015, (2006).

(6) Vogt, S.; Landoni, C., "Monitoring acidic and basic contamination in leading edge lithography and metrology applications: quantitative comparison of solid-state and impinger based sampling methods.", *Proceedings of SPIE, Metrology, Inspection and Process Control for Microlithography XXIV*, Vol. 7638, pp. 7638, 763825-7, (2010).

(7) Giguère P. and Turrell, S., "The nature of hydrofluoric acid: A spectroscopic study of the proton-transfer complex $H_3O^+$... $F^-$", *Journal of the American Chemistry Society*, 102 (17), pp. 5473, (1980).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A liquid-free trap for trace levels of an acidic or basic airborne molecular contaminant in a gas, comprising:
   a housing, comprising an inlet and an outlet;
   a flow path between the inlet and the outlet; and
   a porous solid mass of rigid sintered hydrophilic material situated in the flow path between the inlet and the outlet and sealed in the housing, the rigid sintered hydrophilic material functionalized with a basic species for trapping an acidic airborne molecular contaminant in the gas or an acidic species for trapping a basic airborne molecular contaminant in the gas.

2. The liquid-free trap of claim 1, wherein the average pore size of the rigid sintered hydrophilic material is from about 1 micron to about 100 microns.

3. The liquid-free trap of claim 1, wherein the rigid sintered hydrophilic material is sintered metal.

4. The liquid-free trap of claim 1, wherein the rigid sintered hydrophilic material is sintered hydrophilic polyethylene, sintered hydrophilic ultrahigh molecular weight polyethylene, sintered hydrophilic polytetrafluoroethylene, sintered hydrophilic polyethersulfone or sintered hydrophilic nylon.

5. The liquid-free trap of claim 1, wherein the basic species is selected from an alkali or alkaline earth metal salt of bicarbonate, carbonate or hydroxide, or a combination thereof.

6. The liquid-free trap of claim 1, wherein the rigid sintered hydrophilic material is functionalized with a polyprotic acid.

7. The liquid-free trap of claim 1, wherein the housing further comprises an upstream component including the inlet, a downstream component including the outlet and a locking nut to secure the upstream component to the downstream component and the housing is polyether ether ketone (PEEK).

8. The liquid-free trap of claim 1, wherein the rigid sintered hydrophilic material is chemically clean.

9. A method for trapping trace levels of an acidic or basic airborne molecular contaminant in a gas stream, comprising:
   passing a gas stream into the inlet through the flow path and out of the outlet of the liquid-free trap of claim 1 at a flow rate and for a period of time sufficient to trap a detectable quantity of the acidic or basic airborne molecular contaminant with the rigid sintered hydrophilic material.

10. The method of claim 9, wherein the period of time is from about 0.5 to about 8 hours.

11. The method of claim 9, wherein the flow rate is greater than zero and less than about 10 liters per minute.

12. The method of claim 9, wherein the gas stream is humidified prior to passing into the inlet of the liquid-free trap.

13. A method for detecting or measuring trace levels of an acidic or basic airborne molecular contaminant in a gas stream, comprising:
  passing a gas stream into the inlet through the flow path and out of the outlet of the liquid-free trap of claim 1 at a flow rate and for a period of time sufficient to trap a detectable quantity of the acidic or basic airborne molecular contaminant with the rigid sintered hydrophilic material;
  desorbing the trapped acidic or basic airborne molecular contaminant from the rigid sintered hydrophilic material, thereby providing a sample; and
  analyzing the sample for trace levels of the acidic or basic airborne molecular contaminant, thereby detecting or measuring trace levels of an acidic or basic airborne molecular contaminant in the gas stream.

14. The method of claim 13, wherein analyzing the sample comprises analyzing the sample using ion chromatography.

15. The method of claim 13, wherein desorbing the trapped acidic or basic airborne molecular contaminant from the rigid sintered hydrophilic material comprises extracting the trapped acidic or basic airborne molecular contaminant from the rigid sintered hydrophilic material using a solvent.

16. The method of claim 15, wherein extracting the trapped acidic or basic airborne molecular contaminant using a solvent comprises ultrasonically treating a mixture of the rigid sintered hydrophilic material and the solvent.

17. The liquid-free trap of claim 1, wherein the housing comprises:
  a hollow, substantially cylindrical upstream component having a longitudinal axis comprising an inner surface, an outer surface, the inlet and an upstream surface, the inner surface having a tapered portion terminating at the upstream surface, the inner surface tapering from the upstream surface to the inlet;
  a hollow, substantially cylindrical downstream component comprising the outlet and a downstream surface; and
  a locking nut to secure the upstream component to the downstream component without causing the upstream and downstream components to rotate with respect to one another, the upstream surface and the downstream surface together creating a space that is sealed from the environment and situated in a flow path between the inlet and the outlet.

18. The liquid-free trap of claim 17, wherein the rigid sintered hydrophilic material is sealed in the housing and situated in the flow path in the space created by the upstream component and the downstream component between the inlet and the outlet.

19. The liquid-free trap of claim 1, wherein the rigid sintered hydrophilic material has a thickness of from about 0.1 centimeters to about 0.65 centimeters.

20. A liquid-free trap for trace levels of a basic airborne molecular contaminant in a gas, comprising:
  a housing, comprising an inlet and an outlet;
  a flow path between the inlet and the outlet; and
  a porous solid mass of rigid sintered hydrophilic material situated in the flow path between the inlet and the outlet and sealed in the housing, wherein the rigid sintered hydrophilic material is hydrophilic ultrahigh molecular weight polyethylene having an average pore size of from about 5 microns to about 50 microns and is functionalized with phosphoric acid.

21. A liquid-free trap for trace levels of an acidic airborne molecular contaminant in a gas, comprising:
  a housing, comprising an inlet and an outlet;
  a flow path between the inlet and the outlet; and
  a porous solid mass of rigid sintered hydrophilic material situated in the flow path between the inlet and the outlet and sealed in the housing, wherein the rigid sintered hydrophilic material is sintered stainless steel having an average pore size of from about 5 microns to about 50 microns and is functionalized with an alkali metal carbonate or bicarbonate.

22. The liquid-free trap of claim 21, wherein the rigid sintered hydrophilic material is functionalized with sodium carbonate or sodium bicarbonate or potassium hydroxide.

* * * * *